(12) United States Patent
Chrzan et al.

(10) Patent No.: US 6,753,409 B1
(45) Date of Patent: Jun. 22, 2004

(54) STABLE NON-HYGROSCOPIC CRYSTALLINE FORM OF N-[N-[N-(4-(PIPERIDIN-4-YL)BUTANOYL)-N-ETHYLGLYCYL]ASPARTYL]-L-β-CYCLOHEXYL ALANINE AMIDE, INTERMEDIATES THEREOF, AND PREPARATION THEREOF AND OF ANTITHROMBOTIC AZACYCLOALKYLALKANOYL PEPTIDES AND PSEUDOPEPTIDES

(75) Inventors: Zofia J. Chrzan, Sellersville, PA (US); James J. Mencel, Lansdale, PA (US); David Toledo-Velasquez, Lansdale, PA (US); Vincent Windisch, Green Lane, PA (US); Rick G. Woodward, Harleysville, PA (US); Diane C. Salazar, deceased, late of Wayne, PA (US), by legal representative Richard C. Salazar; Narasimha M. Vemuri, Phoenixville, PA (US); Anthony J. Gardetto, Oley, PA (US); Matthew R. Powers, Barto, PA (US); Gregory G. Kubiak, Wilmington, DE (US); Robert C. Liu, Walnut Creek, CA (US); Benoit J. Vanasse, Collegeville, PA (US); James P. Sherbine, Voorhees, NJ (US); Walter Rodriguez, Douglasville, PA (US); Adam W. Sledeski, Collegeville, PA (US)

(73) Assignee: Aventis Pharmaceuticals Inc., Bridgewater, NJ (US)

( * ) Notice: Subject to any disclaimer, the term of this patent is extended or adjusted under 35 U.S.C. 154(b) by 91 days.

(21) Appl. No.: 09/639,634

(22) Filed: Aug. 15, 2000

Related U.S. Application Data

(62) Division of application No. 09/251,030, filed on Feb. 18, 1999, now Pat. No. 6,153,588, which is a continuation of application No. PCT/US97/14756, filed on Aug. 21, 1997.
(60) Provisional application No. 60/024,284, filed on Aug. 21, 1996, now abandoned.

(51) Int. Cl.[7] ................................................. C07K 5/08
(52) U.S. Cl. .......................... 530/331; 530/333; 514/19
(58) Field of Search ................................. 530/331, 333; 514/19, 18

(56) References Cited

U.S. PATENT DOCUMENTS

| | | | |
|---|---|---|---|
| 4,857,508 A | 8/1989 | Adams et al. | 514/18 |
| 4,952,562 A | 8/1990 | Klein et al. | 514/18 |
| 4,992,463 A | 2/1991 | Tjoeng et al. | 514/438 |
| 5,064,814 A | 11/1991 | Klein et al. | 514/18 |
| 5,218,138 A | 6/1993 | Chiu et al. | 560/60 |
| 5,264,420 A | 11/1993 | Duggan et al. | 514/19 |
| 5,332,726 A | 7/1994 | Klein et al. | 514/18 |
| 5,340,798 A | 8/1994 | Nutt et al. | 514/18 |
| 5,607,948 A | 3/1997 | Ikeda et al. | 514/316 |
| 5,707,994 A | 1/1998 | Ikeda et al. | 514/255 |
| 5,780,590 A * | 7/1998 | Klein | 530/331 |
| 5,866,685 A * | 2/1999 | Klein | 530/331 |
| 6,048,854 A | 4/2000 | Ikeda et al. | 514/213 |
| 6,153,588 A * | 11/2000 | Chrzan | 514/18 |
| 6,180,759 B1 * | 1/2001 | Mencel | 530/330 |

FOREIGN PATENT DOCUMENTS

| | | |
|---|---|---|
| EP | 0 478 362 | 4/1992 |
| WO | WO 95/10295 | 4/1995 |

\* cited by examiner

*Primary Examiner*—Christopher S. F. Low
*Assistant Examiner*—David Lukton
(74) *Attorney, Agent, or Firm*—Raymond S. Parker, III; Jiang Lin; Irving Newman

(57) ABSTRACT

The invention is directed to a non-hygroscopic stable crystalline form of the antithrombotic compound N-[N-[N-(4-piperdin-4-yl)butanoyl)-N-ethylglycyl]-(L)-aspartyl]-(L)-β-cyclohexyl-alanine amide, to processes for preparing said stable crystalline form, to a pharmaceutical composition thereof, and intermediates thereof, and the invention is directed also to processes for preparing a compound of the formula

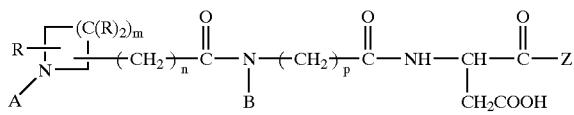

wherein:
A, B, Z, E$^1$, E$^2$, G, R, m, n, and p are as defined herein.

17 Claims, 9 Drawing Sheets

STABLE NON-HYGROSCOPIC CRYSTALLINE FORM OF N-[N-[N-(4-(PIPERIDIN-4-YL)BUTANOYL)-N-ETHYLGLYCYL]ASPARTYL]-L-β-CYCLOHEXYL ALANINE AMIDE, INTERMEDIATES THEREOF, AND PREPARATION THEREOF AND OF ANTITHROMBOTIC AZACYCLOALKYLALKANOYL PEPTIDES AND PSEUDOPEPTIDES

CROSS REFERENCE TO RELATED APPLICATIONS

This application is a divisional of U.S. patent application Ser. No. 09/251,030, filed Feb. 18, 1999, now U.S. Pat. No. 6,153,588 which is a continuation of International Patent Application No. PCT/US97/14756, filed Aug. 21, 1997, which claims benefit of U.S. Ser. No. 60/024,284 filed Aug. 21, 1996, now abandoned.

BACKGROUND OF INVENTION

1. Field of the Invention

The invention is directed to a non-hygroscopic stable crystalline form of N-[N-[N-(4-piperdin-4-yl)butanoyl)-N-ethylglycyl]-(L)-aspartyl]-(L)-β-cyclohexyl-alanine amide of formula I. The compound has antithrombotic activity,

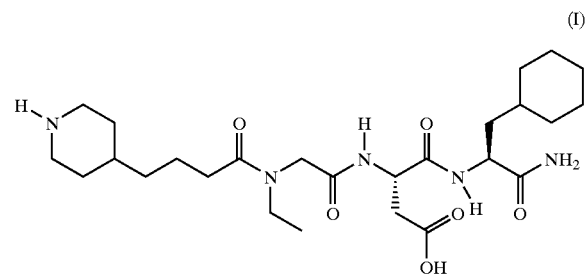

(I)

including the inhibition of platelet aggregation and thrombus formation in mammals, and is useful in the prevention and treatment of thrombosis associated with disease states such as myocardial infarction, stroke, peripheral arterial disease and disseminated intravascular coagulation.

In addition, the invention is directed to processes for preparing the crystalline form of N-[N-[N-(4-piperdin-4-yl)butanoyl)-N-ethylglycyl]-(L)-aspartyl]-(L)-β-cyclohexyl-alanine amide, a pharmaceutical composition thereof and intermediates thereof.

Haemostasis, the biochemistry of blood coagulation, is an extremely complex phenomena whereby normal whole blood and body tissue spontaneously arrest bleeding from injured blood vessels. Effective haemostasis requires the combined activity of vascular, platelet and plasma factors as well as a controlling mechanism to prevent excessive clotting. Defects, deficiencies, or excesses of any of these components can lead to hemorrhagic or thrombotic consequences.

Platelet adhesion, spreading and aggregation on extracellular matrices are central events in thrombus formation. These events are mediated by a family of adhesive glycoproteins, i.e., fibrinogen, fibronectin, and von Willebrand factor. Fibrinogen is a co-factor for platelet aggregation, while fibronectin supports platelet attachments and spreading reactions, and von Willebrand factor is important in platelet attachment to and spreading on subendothelial matrices. The binding sites for fibrinogen, fibronectin and von Willebrand factor have been located on the platelet membrane protein complex known as glycoprotein IIb/IIIa.

Adhesive glycoproteins, like fibrinogen, do not bind with normal resting platelets. However, when a platelet is activated with an agonist such as thrombin or adenosine diphosphate, the platelet changes its shape, perhaps making the GPIIb/IIIa binding site accessible to fibrinogen. The compound within the scope of the present invention blocks the fibrinogen receptor, and thus has the aforesaid antithrombotic activity.

2. Reported Developments

It has been observed that the presence of Arg-Gly-Asp (RGD) is necessary in fibrinogen, fibronectin and von Willebrand factor for their interaction with the cell surface receptor (Ruoslahti E., Pierschbacher, *Cell* 1986, 44, 517–18). Two other amino acid sequences also seem to take part in the platelet attachment function of fibrinogen, namely, the, Gly-Pro-Arg sequence, and the dodecapeptide, His-His-Leu-Gly-Gly-Ala-Lys-Gln-Ala-Gly-Asp-Val sequence (SEQ ID NO: 1). Small synthetic peptides containing the RGD or dodecapeptide have been shown to bind to the platelet GPIIb/IIIa receptor and competitively inhibit binding of fibrinogen, fibronectin and von Willebrand factor as well as inhibit aggregation of activated platelets (Plow, et al., *Proc. Natl. Acad. Sci. USA* 1985, 82, 8057–61; Ruggeri, et al., *Proc. Natl. Acad. Sci. USA* 1986, 5708–12;

Ginsberg, et al., *J. Bio. Chem.* 1985, 260, 3931–36; and Gartner, et al., *J. Biol. Chem.* 1987, 260, 11,891–94).

Indolyl compounds containing guanidinoalkanoyl- and guandinoalkenoyl-aspartyl moieties are reported to be platelet-aggregation inhibitors by Tjoeng, et al., U.S. Pat. Nos. 5,037,808 and 4,879,313.

U.S. Pat. No. 4,992,463 (Tjoeng, et al.), issued Feb. 12, 1991, discloses generically that a series of aryl and aralkyl guanidinoalkyl peptide mimetic compounds exhibit platelet aggregation inhibiting activity and discloses specifically a series of mono- and dimethoxy phenyl peptide mimetic compounds and a biphenylalkyl peptide mimetic compound.

U.S. Pat. No. 4,857,508 (Adams, et al.), issued Aug. 15, 1989, discloses generically that a series of guandinoalkyl peptide derivatives containing terminal aralkyl substituents exhibit platelet aggregation inhibiting activity and discloses specifically a series of O-methyl tyrosine, biphenyl, and naphthyl derivatives containing a terminal amide functionality.

Haverstick, D. M. et al., in *Blood* 66 (4), 946–952 (1985), disclose that a number of synthetic peptides, including arg-gly-asp-ser (SEQ ID NO:2) and gly-arg-gly-asp-ser (SEQ ID NO:3), are capable of inhibiting thrombin-induced platelet aggregation.

Plow, E. F. et al. in *Proc. Nati. Acad Sci. USA* 79, 3711–3715 (1982), disclose that the tetrapeptide glycyl-L-prolyl-L-arginyl-L-proline (SEQ ID NO:4) inhibits fibrinogen binding to human platelets.

French Application No. 86/17507, filed Dec. 15, 1986, discloses that tetra-, penta- and hexapeptide derivatives containing the —arg-gly-asp-sequence are useful as antithrombotics.

U.S. Pat. No. 4,683,291 (Zimmerman, et al.), issued Jul. 28, 1987, discloses that a series of peptides, comprised of from six to forty amino acids, which contain the sequence —arg-gly-asp— are platelet binding inhibitors.

European Application Publication No. 0 319 506, published Jun. 7, 1989, discloses that a series of tetra-, penta-, and hexapeptide derivatives containing the —arg-gly-asp-sequence are platelet aggregation inhibitors.

Cyclic peptide analogues containing the moiety Gly-Asp are reported to be fibrinogen receptor antagonists in U.S. Pat. No. 5,023,233.

Peptides and pseudopeptides containing amino-, guanidino-, imidizaloyl, and/or amidinoalkanoyl, and alkenoyl moieties are reported to be antithrombotic agents in pending U.S. application Ser. Nos. 07/677,006, 07/534,385, and 07/460,777 filed on Mar. 28, 1991, Jun. 7, 1990, and Jan. 4, 1990, respectively, now abandoned, as well as in U.S. Pat. No. 4,952,562, and in International Application No. PCT/US90/05448, filed Sep. 25, 1990, all assigned to the same assignee as the present invention.

Peptides and pseudopeptides containing amino- and guanidino- alkyl- and alkenyl-benzoyl, phenylalkanoyl, and phenylalkenoyl moieties are reported to be antithrombotic agents in pending U.S. application Ser. No. 07/475.043, filed Feb. 5, 1990, and in International Application No. PCT/US91/02471, filed Apr. 11, 1991, published as International Publication No. WO 92/13117 Oct. 29, 1992, assigned to the same assignee as the present invention.

Alkanoyl and substituted alkanoyl azacycloalkylformyl aspartic acid derivatives are reported to be platelet aggregation inhibitors in U.S. Pat. No. 5,053,392, filed Dec. 1, 1989, and assigned to the same assignee and having the same inventorship as the present invention.

N-subsituted azacycloalkylcarbonyl cyclic aminoacylaspartic acid derivatives are reported to be antithrombotics in U.S. Pat. No. 5,064,814, filed Apr. 5, 1990 by the same inventors and assigned to the same assignee as the present invention. Azacycloalkylformylglycyl aspartic acid derivatives are reported to be antithrombotics in U.S. Pat. No. 5,051,405, filed Oct. 10, 1989, and assigned to the same assignee as the present invention.

European Patent Application 0 479 481, published Apr. 8, 1992, discloses azacycloalkyalkanoyl glycyl aspartyl amino acids as fibrinogen receptor antagonists.

European Patent Application 0 478 362, published Apr. 1, 1992, discloses azacycloalkyalkanoyl peptidyl β-alanines as fibrinogen receptor antagonists.

PCT Patent Application Publication No. WO95/10295 discloses azacycloalkylalkanoyl peptides and pseudopeptides of formula II and, in

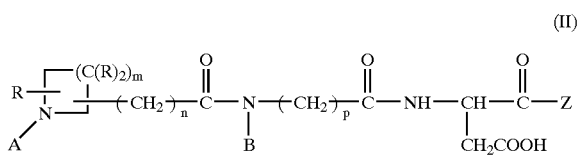

particular, N-[N-[N-(4-(piperdin-4-yl)butanoyl)-N-ethylglycyl]-(L)-aspartyl]-(L)-β-cyclohexylaianine amide that inhibit platelet aggregation and thrombus formation in mammals and are useful in the prevention and treatment of thrombosis. The N-[N-[N-(4-(piperdin-4-yl)butanoyl)-N-ethylglycyl]-(L)-aspartyl]-(L)-β-cyclohexylalanine amide prepared according to PCT Patent Application Publication No. WO95/10295 is amorphous, hygroscopic and is physically unstable as it absorbs moisture. PCT Patent Application Publication No. WO95/10295 does not disclose a non-hygroscopic stable crystalline form of N-[N-[N-(4-piperdin-4-yl)butanoyl)-N-ethylglycyl]-(L)-aspartyl]-(L)-β-cyclohexyl-alanine amide.

PCT Patent Application Publication No. WO95/10295 also discloses that the azacycloalkylalkanoyl peptides and pseudopeptides are prepared generally by standard solid phase or solution phase peptide synthesis procedures using starting materials and/or readily available intermediates from chemical supply companies such as Aldrich or Sigma, (H. Paulsen, G. Merz, V. Weichart, "Solid-Phase Synthesis of O-Glycopeptide Sequences". Angew. Chem. Int. Ed. Engl. 27 (1988); H. Mergler, R. Tanner, J. Gosteli, and P. Grogg. "Peptide Synthesis by a Combination of Solid-Phase and Solution Methods 1: A New Very Acid-Labile Anchor Group for the Solid-Phase Synthesis of Fully Protected Fragments. Tetrahedron letters 29, 4005 (1988); Merrifield, R. B., "Solid Phase Peptide Synthesis after 25 Years: The Design and Synthesis of Antagonists of Glucagon". Makromol. Chem. Macromol. Symp. 19, 31 (1988)). Furthermore, PCT Patent Application Publication No. WO95/10295 discloses that the amorphous and hygroscopic form of N-[N-[N-(4-piperdin-4-yl)butanoyl)-N-ethylglycyl]-(L)-aspartyl-(L)-β-cyclohexylalanine amide is prepared by sequential synthesis from the C-terminus amino acid as shown in Scheme I. PCT Patent Scheme I

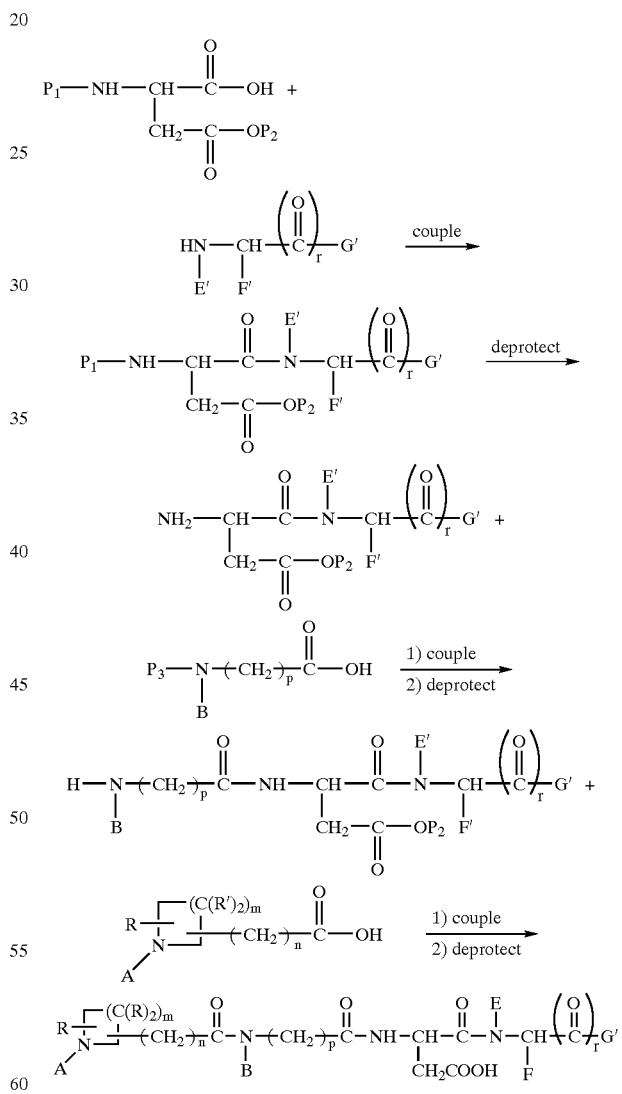

Application Publication No. WO95/10295 does not disclose the formation of tetra-azacycloalkylalkanoyl peptides and pseudopeptides or, in particular, N-[N-[N-(4-piperdin-4-yl) butanoyl)-N-ethylglycyl]-(L)-aspartyl]-(L)-β-cyclohexyl-alanine amide from a central di(pseudopeptide or peptide) whereby the N- and C-Terminal ends of the central di(pseudopeptide or peptide) are both coupled with pseudoamino acids and/or aminoacids to form the tetra-azacycloalkyl-alkanoyl peptides and pselidopeptides.

SUMMARY OF THE INVENTION

The present invention is directed to a non-hygroscopic stable crystalline form of N-[N-[N-(4-piperdin-4-yl)butanoyl)-N-ethylglycyl]-(L)-aspartyl]-(L)-β-cyclohexylalanime amide of formula I. The compound has antithrombotic

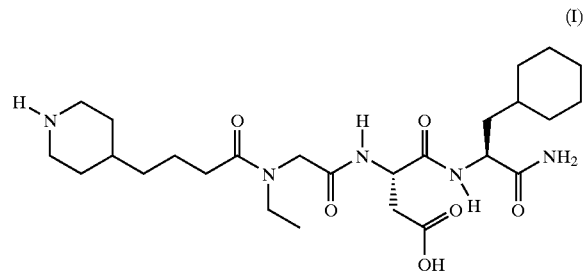

activity, including the inhibition of platelet aggregation and thrombus formation in mammals, and is useful in the prevention and treatment of thrombosis associated with disease states such as myocardial infarction, stroke, peripheral arterial disease and disseminated intravascular coagulation. The invention is also directed to a pharmaceutical composition of the non-hygroscopic stable crystalline form of N-[N-[N-(4-piperdin-4-yl)butanoyl)-N-ethylglycyl]-(L)-aspartyl]-(L)-β-cyclohexylaianine amide and intermediates thereof.

The invention is also directed to processes for preparing a tetra-azacycloalkylalkanoyl peptide or pseudopeptide compound of formula II

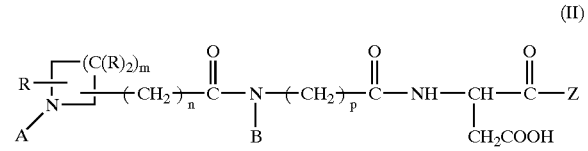

wherein:

A is H;

B is alkyl, cycloalkyl, cycloalkylalkyl, alkylcycloalkyl, alkylcycloalkylalkyl, aryl, aralkyl, alkylaryl, or alkylaralkyl;

Z is

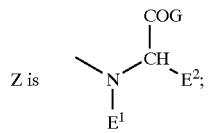

$E^1$ is H;

$E^2$ is the a-carbon side chain of a naturally occuring a-amino acid, H, alkyl, cycloalkyl, cycloalkylalkyl, alkylcycloalkyl, alkylcycloalkylalkyl, aryl, substituted aryl, aralkyl, substitued aralkyl, heterocyclyl, substituted heterocyclyl, heterocyclylalkyl, substituted heterocyclylalkyl, or $E^1$ and $E^2$ taken together with the nitrogen and carbon atoms through which $E^1$ and $E^2$ are linked form a 4-, 5-, 6-, or 7-membered azacycloalkane ring;

G is $OR^1$ or $NR^1R^2$;

$R^1$ and $R^2$ are independently H, alkyl, cycloalkyl, cycloalkylalkyl, alkylcycloalkyl, alkylcycloalkylalkyl, aryl, aralkyl, alkylaryl, or alkylaralkyl;

R is H, alkyl, aryl, or aralkyl;

m is 1 to 5;

n is 0 to 6; and p is 1 to 4, and, in particular, the non-hygroscopic stable crystalline form of N-[N-[N-(4-piperdin-4-yl)butanoyl)-N-ethylglycyl]-(L)-aspartyl]-(L)-β-cyclohexylalanine amide.

BRIEF DESCRIPTION OF THE FIGURES

FIG. 9 represents that the hygroscopic form picks up more water than the non-hygroscopic form as the RH increases, and more pronounced at relative humidities greater than 60%. Furthermore, FIG. 9 represents that the hygroscopic form of the compound does not desorb to its original weight % whereas the non-hygroscopic form of the compound does desorb to its original weight %.

DETAILED DESCRIPTION OF THE INVENTION

Figure 1:
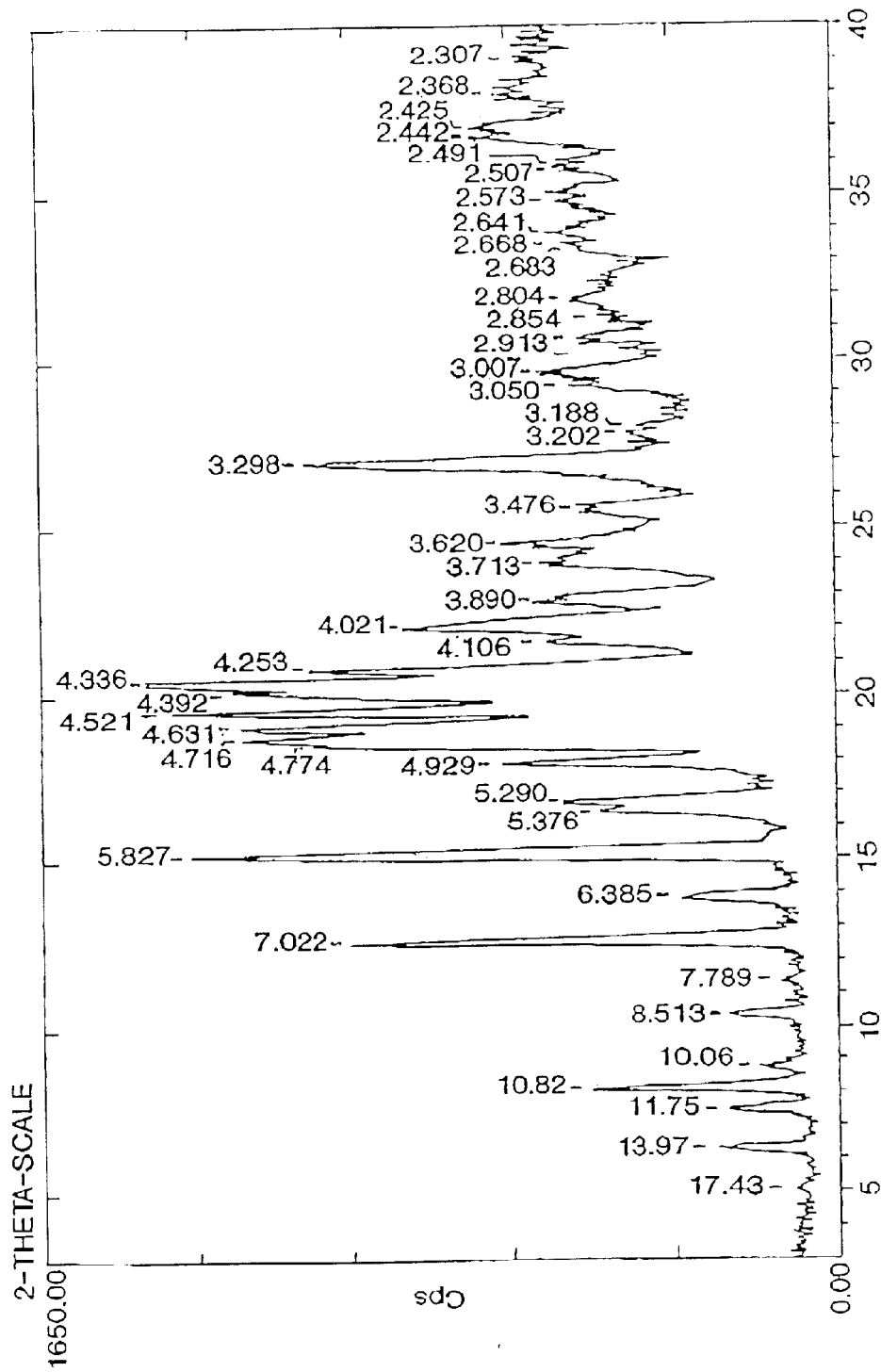
FIG. 1 represents a x-ray powder diffraction graph of a sample of the non-hygroscopic crystalline form of N-[N-[N-(4-piperdin-4-yl)butanoyl)-N-ethylglycyl]-(L)-aspartyl]-(L)-β-cyclohexylalanine amide prepared in Example 13, Method A.

As used above, and throughout the description of this invention, the following terms, unless otherwise indicated, shall be understood to have the following meanings:

The following abbreviations used herein include: BOC (t-butyloxycarbonyl), CBZ (benzyloxycarbonyl), Gly (glycine), Asp (aspartic acid), Obzl (benzyloxy), TFA (trifluoroacetic acid), Cha(β-cyclohexyl-alanine), EtOAc (ethyl acetate), DMF (dimethyl formamide), DCC (dicyclohexylcarbodiimide), HOBT (hydroxybenzotriazole), TBTU (2-1 H-Benzotriazol-1-yl)-1,1.3,3-tetramethyluronium tetrafluoroborate), DI (deionized water), PNP (p-nitrophenol), PFP (pentafluorophenol), DCU (dicyclohexyl urea), NMM (N-methylmorpholine), MTBE (methyl t-butyl ether), RH (relative humidity), THF (tetrahydrofuran) PipBu (4-piperidinebutyric acid) and PipBuen((4-piperidinebutylidenylcarboxylic acid) is a compound of the formula

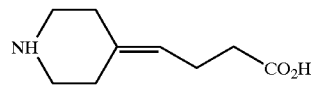

"Patient" includes both human and other mammals. "Pharmaceutically acceptable salt" means a salt form of the parent compound of formula I which is relatively innocuous to a patient when used in therapeutic doses so that the beneficial pharmaceutical properties of the parent compound of formula I are not vitiated by side-effects ascribable to a counter ion of that salt form. Pharmaceutically acceptable salt also includes a zwitterion or internal salt of the compound of formula I.

"Alkyl" means a saturated aliphatic hydrocarbon group which may be straight or branched and having about 1 to about 20 carbon atoms in the chain. Branched means that a lower alkyl group such as methyl, ethyl or propyl is attached to a linear alkyl chain. Preferred straight or branched alkyl groups are the "lower alkyl" groups which are those alkyl groups having from 1 to about 10 carbon atoms. Most preferred lower alkyl groups have from 1 to about 6 carbon atoms.

"Cycloalkyl" means a saturated carbocyclic group having one or more rings and having about 3 to about 10 carbon atoms. Preferred cycloalkyl groups include cyclopropyl, cyclobutyl, cyclopentyl, cyclohexyl, cycloheptyl, and decahydronaphthyl.

"Cycloalkylalkyl means an alkyl group substituted with a cycloalkyl group. Preferred cycloalkylalkyl groups include cyclopentylmethyl, cyclohexylmethyl, cyclohexylethyl, decahydronaphth-1-ylmethyl and decahydronaphth-2-ylmethyl.

"Alkylcycloalkyl" means an cycloalkyl group substituted with an alkyl group. Exemplary alkylcycloalkyl groups include 1-, 2-, 3-, or 4-methyl or ethyl cyclohexyl.

"Alkylcycloalkylalkyl" means an alkyl group substituted by an alkylcycloalkyl group. Exemplary alkylcycloalkyl groups include 1-, 2-, 3-, or 4-methyl or ethyl cyclohexyl-methyl or 1-, 2-, 3-, or ethyl cyclohexylethyl.

"Azacycloalkane" means a saturated aliphatic ring containing a nitrogen atom. Preferred azacycloalkanes include pyrolidine and piperidine.

"Naturally occuring α-amino acid" means glycine, alanine, valine, leucine. isoleucine, serine, threonine, phenylalanine, tyrosine, tryptophan, cysteine, methionine, proline, hydroxyproline, aspartic acid, asparagine, glutamine, glutamic acid, histidine, arginine, ornithine, and lysine.

"α-carbon side chain of a naturally occuring α-amino acid" means the moiety which substitutes the α-carbon of a naturally occuring α-amino acid. Exemplary α-carbon side chains of naturally occuring α-amino acids include isopropyl, methyl, and carboxymethyl for valine, alanine, and aspartic acid, respectively.

The term "amine protecting group" means an easily removable group which is known in the art to protect an amino group against undesirable reaction during synthetic procedures and to be selectively removable. The use of amine protecting groups is well known in the art for protecting groups against undesirable reactions during a synthetic procedure and many such protecting groups are known, cf, for example, T. H. Greene and P. G. M. Wuts, Protective Groups in Organic Synthesis, 2nd edition, John Wiley & Sons, New York (1991), incorporated herein by reference. Preferred amine protecting groups are acyl, including formyl, acetyl, chloroacetyl, trichloroacetyl, o-nitrophenylacetyl, o-nitrophenoxyacetyl, trifluoroacetyl, acetoacetyl, 4-chlorobutyryl, isobutyryl, o-nitrocinnamoyl, picolinoyl, acylisothiocyanate, aminocaproyl, benzoyl and the like, and acyloxy including methoxycarbonyl, 9-fluorenylmethoxycarbonyl, 2,2,2-trifluoroethoxycarbonyl, 2-trimethylsilylethxoycarbonyl, vinyloxycarbonyl, allyloxycarbonyl, t-butyloxycarbonyl (BOC), 1,1-dimethylpropynyloxycarbonyl, benzyloxycarbonyl (CBZ), p-nitrobenzyloxycarbony, 2,4-dichlorobenzyloxycarbonyl, and the like.

The term "acid labile amine protecting group" means an amine protecting group as defined above which is readily removed by treatment with acid while remaining relatively stable to other reagents. A preferred acid labile amine protecting group is tert-butoxycarbonyl (BOC).

The term "hydrogenation labile amine protecting group" means an amine protecting group as defined above which is readily removed by hydrogenation while remaining relatively stable to other reagents. A preferred hydrogenation labile amine protecting group is benzyloxycarbonyl (CBZ).

The term "acid protecting group" means an easily removable group which is known in the art to protect a carboxylic acid (—CO$_2$H) group against undesirable reaction during synthetic procedures and to be selectively removable. The use of carboxylic acid protecting groups is well known in the art and many such protecting groups are known, cf. for example, T. H. Greene and P. G. M. Wuts, Protective Groups in Organic Synthesis, 2nd edition, John Wiley & Sons, New York (1991), incorporated herein by reference. Examples of carboxylic acid protecting groups include esters such as methoxymethyl, methylthiomethyl, tetrahydropyranyl, benzyloxymethyl, substituted and unsubstituted phenacyl, 2,2,2-trichloroethyl, tert-butyl, cinnamyl, substituted and unstibstituted benzyl, trimethylsilyl, and the like, and amides and hydrazides including N,N-dimethyl, 7-nitroindolyl, hydrazide, N-phenylhydrazide, and the like.

The term "hydrogenation labile acid protecting group" means an acid protecting group as defined above which is readily removed by hydrogenation while remaining relatively stable to other reagents. A preferred hydrogenation labile acid protecting group is benzyl.

"Aryl" means a phenyl or naphthyl group.

"Substituted aryl" means a phenyl or naphthyl group substituted by one or more aryl group substitutents which may be the same or different, where "aryl group substituent" includes alkyl, alkenyl, alkynyl, aryl, aralkyl, hydroxy, alkoxy, aryloxy, aralkoxy, hydroxyalkyl, acyl, formyl, carboxy, alkenoyl, aroyl, halo, nitro, trihalomethyl, cyano, alkoxycarbonyl, aryloxycarbonyl, aralkoxycarbonyl, acylamino, aroylamino, carbamoyl, alkylcarbamoyl, dialkylcarbamoyl, arylcarbamoyl, aralkylcarbamoyl, alkylsulfonyl, alkylsulfinyl, arylsulfonyl, arylsulfinyl, aralkylsulfonyl, aralkylsulfinyl, or —NR$_a$R$_b$ where R$_a$ and R$_b$ are independently hydrogen, alkyl, aryl, or aralkyl.

"Aralkyl" means an alkyl group substituted by an aryl radical. Preferred aralkyl groups include benzyl, naphth-1-ylmethyl naphth-2-ylmethyl, and phenethyl.

"Substituted aralkyl" means an aralkyl group substituted on the aryl portion by one or more aryl group substituents.

"Heterocyclyl" means about a 4- to about a 15-membered monocyclic or multicyclic ring system in which one or more of the atoms in the ring is an element other than carbon, for example nitrogen, oxygen, or sulfur. Preferred heterocyclyl groups include pyridyl, pyrimidyl, and pyrrolidyl.

"Substituted heterocyclyl" means a heterocyclyl group substitued by one or more aryl group substituents.

"Heterocyclylalkyl" and "substituted heterocyclylalkyl" means an alkyl group which is substituted by a heterocyclyl and substituted heterocyclyl group, respectively.

"Hygroscopicity" means sorption, implying an acquired amount or state of water sufficient to affect the physical or chemical properties of the substance (Eds. J. Swarbrick and J. C. Boylan, Encyclopedia of Pharmaceutical Technology, Vol. 10, p. 33).

Preferred Embodiments

A preferred compound prepared according to the present invention is described by formula II wherein E$^2$ is H, alkyl, hydroxymethyl, 1-hydroxyethyl, mercaptomethyl, 2-methylthioethyl, carboxymethyl, 2-carboxyethyl, 4-aminobutyl, 3-guanidinopropyl, cycloalkyl, cycloalkylalkyl, alkylcycloalkyl, alkylcycloalkylalkyl, aryl, substituted aryl, aralkyl, substituted aralkyl, heterocyclyl, substituted heterocyclyl, heterocyclylalkyl, substituted heterocyclylalkyl, or E$^1$ and E$^2$ taken together with the nitrogen and carbon atoms through which E$^1$ and E$^2$ are linked form a 4-, 5-, 6-, or 7-membered azacycloalkane ring, provided that heterocyclylalkyl is other than indol-3-ylmethyl.;

A more preferred compound prepared according to the present invention is described by formula II wherein E$^2$ is H, alkyl, hydroxymethyl, 1-hydroxyethyl, mercaptomethyl, 2-methylthioethyl, carboxymethyl, 2-carboxyethyl, 4-aminobutyl, 3-guanidinopropyl, cycloalkyl, cycloalkylalkyl, alkylcycloalkyl, alkylcycloalkylalkyl, aryl, substituted aryl, aralkyl, substituted aralkyl, or E$^1$ and E$^2$ taken together with the nitrogen and carbon atoms through which El and E$^2$ are linked form a 4-, 5-, 6-, or 7-membered azacycloalkane ring.

A still more preferred compound prepared according to the present invention is described by formula II wherein E$^2$ is H, alkyl, hydroxymethyl, 1-hydroxyethyl, mercaptomethyl, 2-methylthioethyl, carboxymethyl, 2-carboxyethyl, 4-aminobutyl, 3-guanidinopropyl, cycloalkyl, cycloalkylalkyl, alkylcycloalkyl, alkylcycloalkylalkyl, or E$^1$ and E$^2$ taken together with the nitrogen and carbon atoms through which E$^1$ and E$^2$ are linked form a 4-, 5-, 6-, or 7-membered azacycloalkane ring.

A further preferred compound prepared according to the present invention is described by formula II wherein B is alkyl, cycloalkyl, cycloalkylalkyl, alkylcycloalkyl, or alkylcycloalkylalkyl.

A special embodiment prepared according to the present invention is described by formula IIa

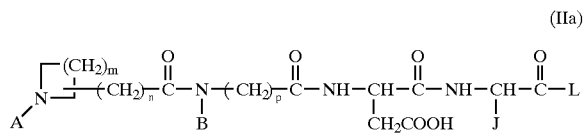

(IIa)

wherein:

B is alkyl, cycloalkyl, cycloalkylalkyl, alkylcycloalkyl, alkylcycloalkylalkyl, aryl, aralkyl, alkylaryl or alkylaralkyl;

J is H, alkyl, cycloalkyl, cycloalkylalkyl, alkylcycloalkyl, alkylcycloalkylalkyl, aryl, substituted aryl, aralkyl or substitued aralkyl;

L is OR$^1$ or NR$^1$$_R$$^2$;

$R^1$ and $R^2$ are independently H, alkyl, cycloalkyl, cycloalkylalkyl, alkylcycloalkyl, alkylcycloalkylalkyl, aryl, aralkyl, alkylaryl or alkylaralkyl;

m is 1 to 5;

n is 2 to 6; and p is 1 or 2.

A more preferred special embodiment prepared according to the present invention is described by formula IIa wherein B is alkyl, cycloalkyl, cycloalkylalkyl, alkylcycloalkyl or alkylcycloalkylalkyl;

J is H, alkyl, cycloalkyl, cycloalkylalkyl, alkylcycloalkyl or alkylcycloalkylalkyl;

m is 3; and n is 3 or 4.

A further preferred special embodiment prepared according to the present invention is described by formula IIa wherein B is alkyl;

J is alkyl, cycloalkyl or cycloalkylalkyl;

$R^1$ and $R^2$ are independently H, alkyl, cycloalkyl, cycloalkylalkyl, alkylcycloalkyl or alkylcycloalkylalkyl;

m is 3;

n is 3 or 4; and p is 1.

A yet further preferred special embodiment prepared according to the present invention is described by formula IIa which is N-[N-[N-(4-piperdin-4-yl)butanoyl)-N-ethylglycyl]-(L)-aspartyl]-(L)-β-cyclohexylalanine amide.

Another embodiment according to the invention is the formation of a stable non-hygroscopic crystalline form of N-[N-[N-(4-piperdin-4-yl)butanoyl)-N-ethylglycyl]-(L)-aspartyl]-(L)-β-cyclohexylalanine amide. According to the invention, this form of the compound is capable of development as a stable formulation of the compound. The stable non-hygroscopic crystalline form of N-[N-[N-(4-piperdin-4-yl)butanoyl)-N-ethylglycyl]-(L)-aspartyl]-(L)-β-cyclohexylalanine amide also has a high melting point and shows no tendency to absorb water. The stable form also exhibits unique and unexpected stability against humidities and temperatures well in excess of those normally encountered upon shipping, dosage form manufacturing, or long tern shippage or storage. These properties also facilitate dosage form manufacturing. The conversion to the stable form also does not result in the loss of material or its purity, and does not adversely affect its particle properties.

It is to be understood that the present invention is intended to cover all combinations of preferred compounds, preferred embodiments and special embodiments as defined herein.

A compound of the present invention is useful in the form of the free base or acid, zwitterionic salt thereof or in the form of a pharmaceutically acceptable salt thereof. All forms are within the scope of the invention.

Where a compound of the present invention is substituted with a basic moiety, an acid addition salt is formed and is simply a more convenient form for use; and in practice, use of the salt form inherently amounts to use of the free base form. The acid which can be used to prepare an acid addition salt includes preferably that which produces, when combined with the free base, a pharmaceutically acceptable salt, that is, a salt whose anion is non-toxic to a patient in the pharmaceutical doses of the salt, so that the beneficial inhibitory effects on platelet aggregation and thrombus formulation inherent in the free base are not vitiated by side effects ascribable to the anion. Although pharmaceutically acceptable salts of said basic compounds are preferred, all acid addition salts are useful as sources of the free base form even if the particular salt, per se, is desired only as an intermediate product as, for example, when the salt is formed only for purposes of purification, and identification, or when it is used as intermediate in preparing a pharmaceutically acceptable salt by ion exchange procedures. Pharmaceutically acceptable salts within the scope of the invention are those derived from the following acids: mineral acids such as hydrochloric acid, sulfuric acid, phosphoric acid and sulfamic acid; and organic acids such as acetic acid, citric acid, lactic acid, tartaric acid, malonic acid, methanesufonic acid. ethanesulfonic acid, benzenesulfonic acid, p-toluenesulfonic acid, cyclohexylsulfamic acid, quinic acid, and the like. The corresponding acid addition salts comprise the following: hydrohalides, e.g., hydrochloride and hydrobromide, sulfate, phosphate, nitrate, sulfamate, acetate, citrate, lactate, tartarate, malonate, oxalate, salicylate, propionate, succinate, fumarate, maleate, methylene-bis-β-hydroxynaphthoates, gentisates, mesylates, isethilonates and di-p-toluoyltartrates-methanesulfonate, ethanesulfonate, benzenesulfonate, p-toluenesulfonate, cyclohexylsulfamate and quinate, respectively.

According to a further feature of the invention, acid addition salts of the compounds of this invention are prepared by reaction of the free base with the appropriate acid, by the application or adaptation of known methods. For example, the acid addition salts of the compounds of this invention are prepared either by dissolving the free base in aqueous or aqueous-alcohol solution or other suitable solvents containing the appropriate acid and isolating the salt by evaporating the solution, or by reacting the free base and acid in an organic solvent, in which case the salt separates directly or can be obtained by concentration of the solution.

The acid addition salts of the compounds of this invention can be regenerated from the salts by the application or adaptation of known methods. For example, parent compounds of the invention can be regenerated from their acid addition salts by treatment with an alkali, e.g., aqueous sodium bicarbonate solution or aqueous ammonia solution.

Where the compound of the invention is substituted with an acidic moiety, base addition salts may be formed and are simply a more convenient form for use; and in practice, use of the salt form inherently amounts to use of the free acid form. The bases which can be used to prepare the base addition salts include preferably those which produce, when combined with the free acid, pharmaceutically acceptable salts, that is, salts whose cations are non-toxic to the animal organism in pharmaceutical doses of the salts, so that the beneficial inhibitory effects on platelet aggregation and thrombus formulation inherent in the free acid are not vitiated by side effects ascribable to the cations. Pharmaceutically acceptable salts, including for example alkali and alkaline earth metal salts, within the scope of the invention are those derived from the following bases: sodium hydride, sodium hydroxide, potassium hydroxide, calcium hydroxide, aluminum hydroxide, lithium hydroxide, magnesium hydroxide, zinc hydroxide, ammonia, ethylenediamine, N-methyl-glucamine, lysine, arginine, ornithine, choline, N,N'-dibenzylethylene-diamine, chloroprocaine, diethanolamiie, procaine, N-benzylphenethylamine, diethylamine, piperazine, tris(hydroxymethyl)-aminomethane, tetramethiylammonium hydroxide, and the like.

Metal salts of compounds of the present invention may be obtained by contacting a hydride, hydroxide, carbonate or similar reactive compound of the chosen metal in an aqueous or organic solvent with the free acid form of the compound. The aqueous solvent employed may be water or it may be a mixture of water with an organic solvent, preferably an alcohol such as methanol or ethanol, a ketone such as acetone, an aliphatic ether such as tetrahydrofuran, or an ester such as ethyl acetate. Such reactions are normally conducted at ambient temperature but they may, if desired, be conducted with heating.

Amine salts of compounds of the present invention may be obtained by contacting an amine in an aqueous or organic solvent with the free acid form of the compound. Suitable aqueous solvents include water and mixtures of water with alcohols such as methanol or ethanol, ethers such as tetrahydrofuran, nitrites such as acetonitrile, or ketones such as acetone. Amino acid salts may be similarly prepared.

The base addition salts of the compounds of this invention can be regenerated from the salts by the application or adaptation of known methods. For example, parent compounds of the invention can be regenerated from their base addition salts by treatment with an acid, e.g., hydrochloric acid.

As well as being useful in themselves as active compounds, salts of compounds of the invention are useful for the purposes of purification of the compounds, for example by exploitation of the solubility differences between the salts and the parent compounds, side products and/or starting materials by techniques well known to those skilled in the art.

Compounds of the present invention may contain asymmetric centers. These asymmetric centers may independently be in either the R or S configuration. It will also be apparent to those skilled in the art that certain compounds of formula I may exhibit geometrical isomerism. Geometrical isomers include the cis and trans forms of compounds of the invention having alkenyl moieties. The present invention comprises the individual geometrical isomers and stereoisomers and mixtures thereof.

Such isomers can be separated from their mixtures., by the application or adaptation of known methods, for example chromatographic techniques and recrystallization techniques, or they are separately prepared from the appropriate isomers of their intermediates, for example by the application or adaptation of methods described herein. U.S. patent application Ser. Nos. 08/138,820 and 08/476,750 now abondoned and which are incorporated herein by reference describe methods for preparing an amorphous compound of formula II, and in particular, an amorphous compound of formula I.

A novel process according to the invention for preparing a compound of formula II, and in particular, a crystalline compound of formula I according to this invention is described by the synthesis shown in Scheme II, wherein B, $E^1$, $E^2$, G, R, m, n and Scheme II

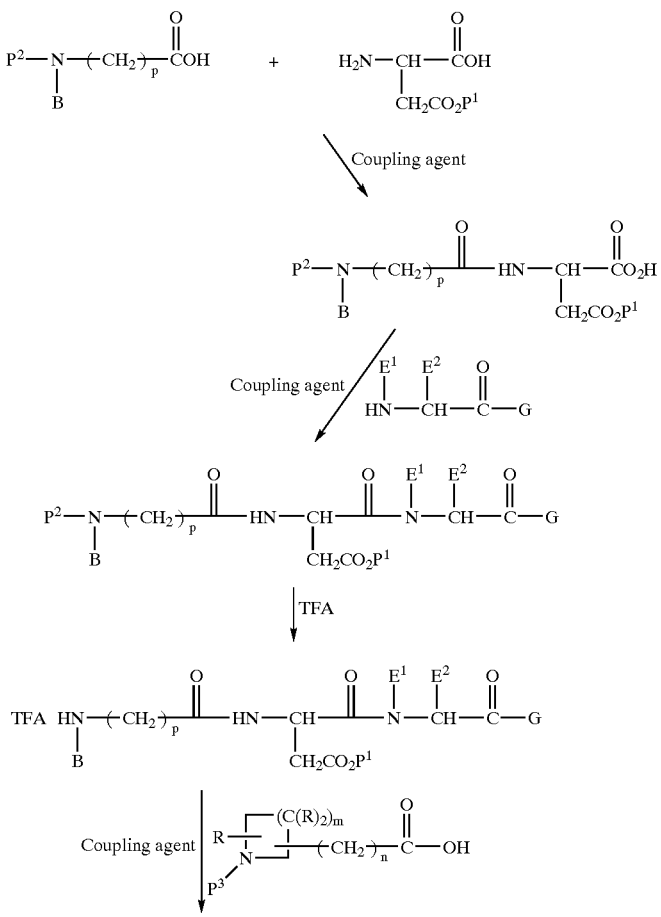

-continued

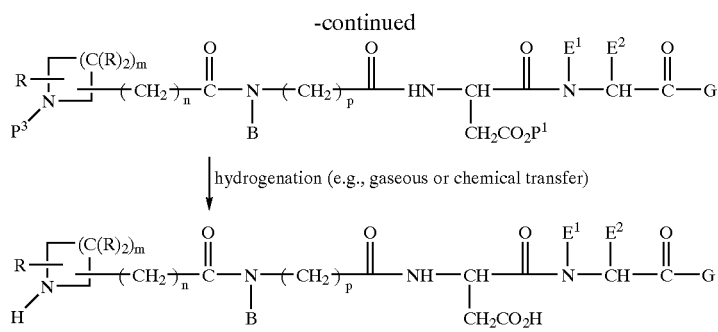

↓ hydrogenation (e.g., gaseous or chemical transfer)

p are as defined above, and $P^1$ is a hydrogenation labile acid protecting group such as benzyl, $P^2$ is an acid labile amine protecting group such as t-butoxycarbonyl (BOC), and $P^3$ is a hydrogenation labile amine protecting group such as benzyloxycarbonyl (CBZ).

During the preparation of compounds of formula II or intermediates thereto, it may also be desirable or necessary to prevent cross-reaction between chemically active substituents on those present on naturally occuring or pseudo amino acids. The substituents may be protected by standard blocking groups which may subsequently be removed or retained, as required, by known methods to afford the desired products or intermediates (see, for example, Green, "Protective Groups in Organic Synthesis", Wiley, N.Y., 1981). Selective protection or deprotection may also be necessary or desirable to allow conversion or removal of existing substituents, or to allow subsequent reaction to affort the final desired product.

The process of Scheme II is exemplified by the preparation of the compound of formula II, however it should be understood that a compound of formula I is prepared using the appropriate starting materials. In the preparation of the compound of formula I according to Scheme II, B is ethyl, $E^1$ is H, $E^2$ is cyclohexylmethyl, G is $NH_2$, R is H, m is 3, n is 3, p is 1, $P^1$ is benzyl, $P^2$ is BOC, and $P^3$ is a CBZ.

An alternative process according to the invention for preparing a compound of formula I is the same as that in Scheme II except that the compound of the formula III, wherein $P^3$ is as defined above, is used in place

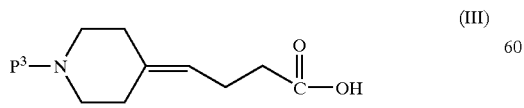 (III)

of the compound of formula IV wherein R is H, m is 3, n is 3, p is 1, and $P^3$ is a

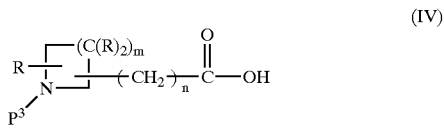 (IV)

CBZ to yield a intermediate of formula V, wherein B is ethyl, $E^1$ is H, $E^2$ is

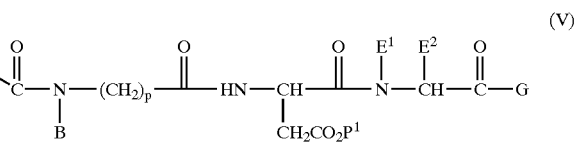 (V)

cyclohexylmethyl, G is $NH_2$, p is 1, $P^1$ is benzyl, and $P^3$ is a CBZ.

Scheme II demonstrates a five step method of preparing a compound according to the invention starting with the formation of a central dipeptide intermediate according to the invention of the formula VI, wherein B, p, $P^2$ and

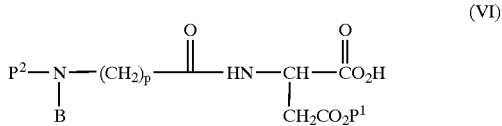 (VI)

$P^1$ are as defined above. In the case of the preparation of the compound of formula I, the central dipeptide intermediate according to the invention is BOC-N(Et)Gly-(L)-Asp (OBzl)—OH. The central dipeptide intermediate is prepared without protection of the free carboxylic acid moiety.

In step 2 of Scheme II, the coupling to form the central dipeptide may be effected in either dichloromethane or mixtures of ethyl acetate—with or without DMF as cosolvent—and organic bases such as NMM, and may be done at about room temperature to about 40° C. Activation of the amino acid or pseudo amino acid of the following formula for coupling may be effected using

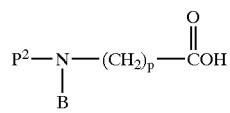

non-isolated active esters with p-nitrophenol, pentafluorophenol, and N-hydroxy-succinimide via the action of dicyclohexylcarbodiimide. Coupling times range from about 1 to about 20 hours, depending upon the amino acids or pseudo amino acids to be coupled, activating agent, solvent, and temperature. The central dipeptide product of step 1 does not have to be isolated. The step 1 reaction mixture is typically washed with water or dilute aqueous acid (eg. aq. HCl), and then used directly without drying in step 2. In the instance when a phenol-based active esters is used, the central dipeptide product is extracted into alkaline water from the reaction mixture. then re-extracted from the acidified aqueous solution back into an organic solvent; and the solution is reacted directly as in step 2.

The dipeptide intermediate of formula VI is used to prepare a tripeptide intermediate according to the invention of formula VII, wherein B, E, F, G, p and

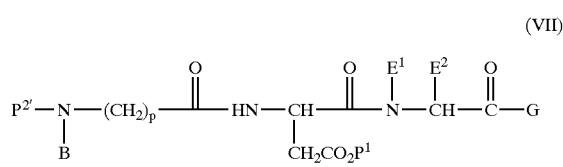
(VII)

$P^1$ are as defined above, and $P^{2'}$ is $P^2$ or TFA.H—. Where $P^{2'}$ is TFA.H—, The "." symbol represents dissociation of the TFA to form $F_3CCO_2^-$ and $H^+$, wherein the $H^+$ protonates the terminal amine in the compound of formula VII, i.e., yielding the TFA salt of formula VIIa. In the case of the preparation of the compound of

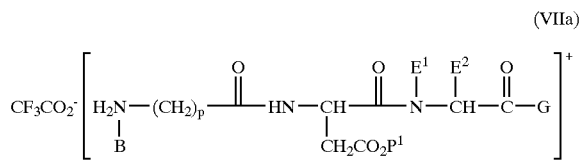
(VIIa)

formula I, the tripeptide intermediate according to the invention is $P^{2'}$—N(Et)Gly-(L)-Asp(OBzl)-(L)-Cha-NH$_2$.

In step 2, the coupling of an amino acid or pseudo amino acid to the central dipeptide may be effected in either dichloromethane or in mixtures of ethyl acetate and DMF or THF, and at about or below room temperature. Activation of the central dipeptide of the following formula for coupling may be

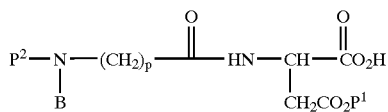

effected using non-isolated active esters of pentafluorophenol or N-hydroxy-succinimide via the action of dicyclohexylcarbodiimide. Activation may also be effected using isopropyl chloroformate. Reaction times vary with the amino acids or pseudo amino acids to be coupled, activating agent, solvent, and temperature, and range from about 1 to about 20 hours. The tripeptide product does not have to be isolated. When the tripeptide intermediate is not isolated, the reaction mixture is washed with aqueous organic base such aq. N-methyl morpholine and aqueous acid such as aq. HCl and is reacted "as is" via the method of Step 3 after the aqueous washings and without drying.

In Step 3 of Scheme II, the removal of the protecting group such as BOC from the tripeptide product of Step 2 may be effected using a solution of trifluoroacetic acid in dichloromethane, or using a mixture of HBr in acetic acid and ethyl acetate. The reaction may be run at about room temperature, and requires about 1 hour (HBr method) and about 2 hours (TFA method). The acid salt product of the tripeptide is isolated by filtration as a crystalline solid either directly form the reaction mixture (HBr method), or after partial solvent removal by distillation and addition of a non-polar solvent to the pot residue.

A further process according to the invention is described as a single concatenated process to rapidly and simply prepare TFA.H—N(Et)Gly-(L)-Asp(OBzl)-(L)-Cha-NH$_2$ from BOC-N(Et)Gly-OH, which process is a one-pot reaction encompassing the first two coupling steps in Scheme II and the treatment with TFA. The TFA.HN(Et)Gly-(L)-Asp(OBzl)-(L)-Cha-NH$_2$ is obtained singularly as it crystallizes directly from the concatenated reaction solution. The concatenated process avoids;the corresponding three discreet reactions in Scheme II and solves the problem to establish a simple, time- and cost-efficient synthesis which is useful in a manufacturing environment.

Scheme II shows the construction of a polypeptide in reverse order, beginning with an N-protected amino acid and then adding successively to the carboxyl terminus, as opposed to the conventional order, in which a polypeptide is constructed by successive amidations at the amine terminus of a protected C-terminus amino acid. This reverse synthetic method according to the invention requires nitrogen protection of only the first amino acid, enabling the use from that point onward of successive amino acids having no protection at either the amine or acid terminus (side chain functional groups excepted). The reverse synthetic method also streamlines production of a compound of formula II, and in particular a compound of formula I, by enabling the use of flow type manufacturing technology as opposed to batch type normally required for solution phase peptide chemistry. The new approach cuts production cost by removing the requirement to purchase amino acids protected at the amine terminus. No special equipment, reagents, or analytical methodology are required.

Another process according to the invention is the formation of stable non-hygroscopic crystalline N-[N-[N-(4-piperdin-4-yl)butanoyl)-N-ethylglycyl]-(L)-aspartyl]-(L)-β-cyclohexylalanine amide reproducibly obtained by a novel solid state conversion from hygroscopic crystalline N-[N-[N-(4-piperdin-4-yl)butanoyl)-N-ethylglycyl]-(L)-aspartyl]-(L)-β-cyclohexylalanine amide prepared by the method as described in Scheme II and the noted alternative reaction steps.

The hygroscopic crystalline form of N-[N-[N-(4-piperdiin-4-yl)butanoyl)-N-ethylglycyl]-(L)-aspartyl]-(L)-β-cyclohexylalanine amide is physically unstable, and is converted upon exposure to conditions of humidity and temperature to the highly stable, non-hygroscopic crystalline form N-[N-[N-(4-piperdin-4-yl)butanoyl)-N-ethylglycyl]-(L)-aspartyl]-(L)-β-cyclohexylalanine amide.

The general conditions according the invention for the conversion from the hygroscopic crystalline form of N-[N-[N-(4-piperdin-4-yl)butanoyl)-N-ethylglycyl]-(L)-aspartyl]-(L)-β-cyclolexylalanine amide to the highly stable, non-hygroscopic crystalline form N-[N-[N-(4-piperdin-4-yl)butanoyl)-N-ethylglycyl]-(L)-aspartyl]-(L)-β-cyclohexylalanine amide have been effected under static and dynamic conditions.

The static procedure according to the invention is described as a static conversion because it involves exposing the hygroscopic crystalline form of N-[N-[N-(4-piperdin-4-yl)butanoyl)-N-ethylglycyl]-(L)-aspartyl]-(L)-β-cyclohexylalanine amide placed in a non-moving vessel such as in vials or trays to certain conditions of temperature and humidity in a controlled environmental chamber. This "static" conversion is performed at temperatures and relative humidities ranging from about 20° C. to about 80° C., more preferably at about 40° C. to about 80° C., and at about 40% to about 100% RH, preferably about 65 to about 80.

The dynamic procedure according to the invention is described as a dynamic conversion because it involves exposing the hygroscopic crystalline form of N-[N-[N-(4-piperdin-4-yl)butanoyl)-N-ethylglycyl]-(L)-aspartyl]-(L)-β-cyclohexylalanine amide under incubation at the humidity and temperature levels as in the static model, but also under a means of agitation, including tumbling of the hygroscopic crystalline form of N-[N-[N-(4-piperdin-4-yl)butanoyl)-N-ethylglycyl]-(L)-aspartyl]-(L)-β-cyclohexylatanine amide in a rotary evaporation flask or in a cylindrical vessel (in a humidity oven) with propeller agitation.

The following Examples are illustrative of the invention and are not intended to limit the scope.

Unless otherwise indicated, reported mass spectral analysis data are Low Resolution Fast Atom Bombardment performed on a VG 70SE with "calculated" values being $(M+H)^+$. Nuclear magnetic resonance (NMR) spectral data is obtained on a Brucker ACF 300, in $D_2O$. Flash chromatography is done on silica gel. High performance liquid chromatography (HPLC) is done on a C-18 Reverse Phase columns of particle size ranging from 8–15μ.

Unless otherwise indicated, reported x-ray powder diffraction graphs are obtained using a Siemens D5000 diffractometer with a Cu radiation source (1.8 kW, 45 kV and 40 mA) to scan powder samples. The samples are milled prior to measurement to eliminate particle size effect on the peak intensities. Approximately 60 mg of the sample are loaded into a 1.5×1 cm sample holder and scanned in the range 3–40° 2 theta (2θ) with step size of 0.04° and the total exposure of 1 second per step.

EXAMPLE 1

Preparation of BOC-N(Et)Gly-(L)-Asp(OBzl)—OH (Step 1 of Scheme II)

Into a 1 L 3-neck round bottom flask are charged 51 g (0.25 mole) of BOC-N(Et)Gly-OH, 35 g (0.25 mole) of PNP, 400 mL of EtOAc, and 100 mL of DMF. The mixture is stirred to form a solution and cooled to 4–6° C. A solution of 51.5 g (0.25 mole) of DCC in 125 mL EtOAc is added dropwise over a period of 10 minutes, while maintaining the temperature from about 5° C. to about 8° C. After all DCC is added, the cooling bath is removed and the mixture is allowed to stir for 1.5 hours as it warmed to room temperature (20–22° C.). A solid precipitate, DCU forms during this period. Completeness of formation of the PNP ester is determined by analytical HPLC (disappearance of BOC-N (Et)Gly-OH). The reaction mixture is filtered and the DCU residue is washed with 2–50 mL portions of EtOAc and the washes added to the filtrate. The DCU is discarded.

To the stirred, filtered solution is added 67 g (0.3 mole) of $H_2N$-(L)-Asp(OBzl)—OH as a slurry in 150 mL (138 g, 1.36 mole) of NMM. The mixture is heated to 38–40° C. and maintained at that temperature for 41 hours, the point at which an analytical HPLC indicates complete consumption of BOC-N(Et)Gly-OPNP. The reaction mixture is cooled to 25° C. and unreacted $H_2N$-(L)-Asp(OBzl)—OH is filtered off. The solution is cooled and refiltered to afford an additional 1.2 g (21.7 g recovered; 11.2 g represents the 20% excess added and 10.5 g (0.047 mole) represents unreacted material).

The filtered solution is extracted in a 2 L Squibb funnel with one portion of 500 mL deionized water, followed with 2–250 mL portions. The combined aq. solution is extracted with 3–300 mL portions of 1:1 MTBE/EtOAc to remove residual PNP (HPLC anal. shows only a trace remaining), then is cooled to 5° C. and acidified from pH 8.9 to pH 1.79 by dropwise addition of 150 mL concentrated HCl. The acidified aqueous solution is extracted with 2–200 mL portions of EtOAc. HPLC analysis of the aqueous shows no residual desired product. The EtOAc extracts are combined, dried over $MgSO_4$, filtered, and concentrated by rotary evaporation at 35° C. The resulting pale orange oil is pumped at 35° C. to maximize removal of residual solvent to afford 85.68 g of BOC-N(Et)Gly-(L)-Asp(OBzl)—OH as an oil (21.3 mmole, 85.5% yield, uncorrected for residual solvent).

Characterization:
NMR (250 MHz): 7.3 ppm (s), 5.1 ppm (s), 3.3 ppm (dq), 3.0 (dq), 1.4 ppm (s), 1.1 (t); MS: M=408; $M+1_{obsvd}$=409 HPLC: 90.79A % (3.87A % p-nitrophenol, uncorrected for e) Elemental analysis: $C_{20}H_{28}N_2O_7$: H, N; $C_{fd}$ 57.54, $C_{cal}$. 58.81

EXAMPLE 2

Preparation of BOC-N(Et)Gly-(L)-Asp(OBzl):-(L)-Cha-$NH_2$ (Step 2 of Scheme II)

Method A: Isopropyl Chloroformate Method

One equivalent BOC-N(Et)Gly-(L)-Asp(OBzl)—OH is dissolved into EtOAc, (6–8 volumes; 1:6.5 Wt:vol) and maintained at a temperature between −15–0° C. NMM (1 equivalent) is added while maintaining the temperature from about −15° C. to about 0° C. Isopropyl chloroformate (1–1.1 equivalents) is added into the protected dipeptide solution at a temperature between −15–0° C. The reaction is maintained at a temperature between about −15° C. to about 0° C. for two to five minutes. A solution of $H_2N$-(L)-Cha-$NH_2$, (1 equivalent), in THF, (10 volumes; 1:10 Wt:vol) is added to the cooled dipeptide solution maintaining temperature at about −15° C. to about 0° C. The reaction is monitored with in-process control (HPLC) samples obtained at 15 minutes, 1 hour, and 2 hours to evaluate reaction completion. (The reaction is complete when the amount of observed dipeptide is less than 10% by area by HPLC analysis.)

The BOC-tripeptide product precipitates directly from the reaction solution and is filtered from the reaction mixture, washed with EtOAc (2×1 volume; Wt:vol), and dried under vacuum. Typical yields are >60%, with purities >90A %; <1A % of the aspartic acid-epimeric diastereomer has been typically observed.

An EtOAc reslurry provides final yields of ~60% of BOC-N(Et)Gly-(L)-Asp(OBzl)-(L)-Cha-$NH_2$ and improves purity to >95A % while reducing the diastercoisomer to <0.5%

As a specific example of the isopropyl chloroformate method, when the general procedure of Example a is followed and 4.55 g (8.1 mmole) of BOC-N(Et)Gly-(L)-Asp (OBzl)—OH is used, then the amount of BOC-N(Et)Gly-(L)-Asp(OBzl)-(L)-Cha-$NH_2$ prepared is 3.26 g (97.9A % pure, 0.3A % diastereomer), a 70% theoretical yield.

Method B: Pentafluoro-Phenol-DCC Complex Method

Pentafluoro phenol (PFP, 2.9 equivalents) and DCC (1 equivalent, are dissolved into EtOAc, (5 volumes; 1:5 Wt:vol) at room temperature and cooled to a temperature between −15–0° C. One equivalent BOC-N(Et)Gly-(L)-Asp (OBzl)—OH is dissolved into EtOAc, (6 volumes; 1:6 Wt:vol) and mixed with one equivalent of $H_2N$-(L)-Cha-$NH_2$ which is previously dissolved into DMF, (10 volumes;

1:10 Wt:vol). The dipeptide/H$_2$N-(L)-Cha-NH$_2$ solution is added dropwise into the solution of PFP and DCC, maintaining temperature between −15–0° C. The reaction is maintained at a temperature between 15–22° C. for five to sixteen hours with in-process control (VIPLC) samples obtained at 1, 2, 3, 4, and 16 hours toevaluate reaction completion. (The reaction is completed when the amount of observed dipeptide is less than 2% by area by HPLC analysis.)

The reaction mixture is filtered and the filter cake (DCU) washed with EtOAc, (2×0.5 volumes; Wt:vol). The filtrate is treated with water, (10 volumes; 1:10 Wt:vol) and the water layer removed. The EtOAc layer is washed with water, (1×, 5 volumes: 1:5 Wt:vol). The EtOAc layer is cooled to precipitate out the product, which is filtered and washed with EtOAc, (2×0.4 volumes; 1:0.4 Wt:vol). Isolated molar yields are >60% with typical purities of >90A %, with 1–4A % of the aspartic acid-epimeric diastereomer.

An EtOAc reslurry provides final yields of ~60% of BOC-N(Et)Gly-(L)-Asp(OBzl)-(L)-Cha-NH$_2$ and improves purity to >99A % while reducing the diastereoisomer to <0.5%.

As a specific example of the pentafluoro-phenol-DCC complex method, when the general procedure of Method B is followed and 10 g (24.5 mmole) of BOC-N(Et)Gly-(L)-Asp(OBzl)—OH is used, then the amount of BOC-N(Et)Gly-(L)-Asp(OBzl)-(L)-Cha-NH$_2$ prepared is 8.15 g (99A % pure, 0.49A % diastereomer), a 59% theoretical yield.

Method C: Hydroxybenzotriazole (HOBT)/2-(1H-Benzotriazol-1-yl)-1,1,3,3-tetramethyluronium Tetrafluoroborate (TBTU) Method One equivalent BOC-N(Et)Gly-(L)-Asp(OBzl)—OH is dissolved in DMF (9–10 volumes; 1:10 Wt:wt) and maintained at ambient temperature. To this solution is added H$_2$N-(L)-Cha-NH1$_2$ (1 equivalent) and hydroxybenzotriazole (HOBT, 1 equiavalent). The resulting solution is cooled to about 0° C. to about 10° C., and NMM (1–1.1 equivalents) is added. The coupling reagent, TBTU, (1–1.1 equivalents) is dissolved into DMF, (4–5 volumes; 1:5 Wt:wt) and is added to the protected dipeptide solution at a temperature of 0° C. to about 10° C. This solution is stirred at about 10° C. to about 25° C. for about 3 hours, until HPLC analysis indicated completion of the reaction (less than 2% starting material by area). The reaction mixture is added to a stirred mixture of 5% aqueous sodium chloride (about 4 volumes vs. reaction volume) and EtOAc (about 2 volumes vs. reaction volume). The phases are separated, and the aqueous phase is extracted with an additional portion of EtOAc (about 1.5 volumes vs. reaction volume). The organic phases are combined and washed sequentially with 0.5 N aqueous citric acid (about 0.6–0.7 volumes vs. organic phase volume), 10% aqueous sodium bicarbonate (twice, with about 0.6–0.7 volumes vs. organic phase volume each) and 25% aqueous sodium chloride (about 0.3–0.4 volumes vs. organic phase volume). The resulting organic phase is concentrated to about ¼ to ½ volume under reduced pressure at about 30–50° C., and to this warm solution is added an equal volume of heptane. The mixture is stirred and allowed to cool to about 0° C. to about 20° C. to precipitate the desired tripeptide. This solid is filtered, washed with a mixture of EtOAc and heptane, and dried. A typical yield is >60%, with typical purities of >95.7 A % and levels of the aspartic acid-epimeric diastereomer at <2A %.

As a specific example of the HOBT/TBTU Method, when the general procedure is followed, 10 g (24.5 mmole) of BOC-N(Et)Gly-(L)-Asp(OBzl)—OH is used, then 9.3 g of BOC-N(Et)Gly-(L)-Asp(OBzl)-(L)-Cha-NH$_2$ is prepared (96.1 A % pure, 1.77A % diastereomer at Asp), a 67.7% theoretical yield.

Mass Spec: M$_{calc}$ 560.7; M+1$_{obsvd}$ 561; mp 182.17 (DSC); $^1$ H NMR (δ vs TMS, D6 DMSO): 0.89 m (1H); 0.94, m (1H); 1.0, dt (2H); 1.15, m (2H); 1.06–1.3, m (4H); 1.36, d (9H); 1.4–1.74, m (6H); 2.65, m (1H); 2.85, m (1H); 3.18, m (2H); 3.75, d (2H); 4.2, s (1H); 4.66, d (1H); 5.08, s(2H); 7.02, s (1H); 7.18, d (1H); 7.36, s (5H); 7.88, dd (1H); 8.24, dd (1H).

EXAMPLE 3

Preparation of TFA.N(Et)Gly-(L)-Asp(OBzl)-(L)-Cha-NH$_2$ (Step 3 of Scheme II)

BOC-N(Et)Gly-(L)-Asp(OBzl)-(L)-Cha-NH$_2$ is dissolved in dichloromethane (~1:12 wt/wt), and to that solution is added TFA at ambient temperature. This is then stirred until HPLC indicates complete reaction (3–5 hours). The solution is concentrated to about ½ volume at 40–45° C. To this warm solution is added MTBE (~1:10 wt/wt vs. BOC-N(Et)Gly-(L)-Asp(OBzl)-(L)-Cha-NH$_2$) while maintaining the temperature >40° C. The mixture is slowly cooled to about 5° C. and stirred for 1 hour to ensure complete crystallization. The resulting solids are filtered, and washed with chilled MTBE. The solids are dried under reduced pressure and analyzed for content of TFA.N(Et)Gly-(L)-Asp(OBzl)-(L)-Cha-NH$_2$ (HPLC wt/wt assay). Yield is generally nearly quantitative, purity >95A %.

Mass Spec: M$_{calc}$. 460 (free base); M+1$_{obsvd}$: 461.

Elemental analysis: C$_{26}$H$_{37}$N$_4$O$_7$F$_3$  H, N, F, C 54.35, fd., 53.82

$^1$H NMR (δ vs TMS, D$^6$ DMSO): 0.9, m (2H); 1.15, t (6H); 1.5, m (1H); 1.5–1.8, m (6H); 2.65 dd (1H); 2.9 m (3H); 3.7, s, (2H); 3.9, m (2H); 4.2, m (1H); 4.75, m (1H); 5.1, s (2H); 7.0, s (1H); 7.15, s (1H); 7.2, s (5H); 8.13, d (1H); 8.7–8.8, m (3H). $^{13}$C NMR (salient signals, δ vs TMS, D6 DMSO): 10.76, 25.49, 25.68, 25.96, 31.66, 33.07, 33.36, 36.25, 38.59, 41.88, 47.02, 49.40, 50.47, 65.71, 127.81–128.34, 135.82, 165.10, 169.34, 173.79

Specific examples of the deprotection are shown in Table A.

TABLE A

| Lab Example | Reaction scale amount (BOC-N(Et)Gly-(L)-Asp(OBzl)-(L)-Cha-NH$_2$.) | Yield and A % purity (TFA.N(Et)Gly-(L)-Asp(OBzl)-(L)-Cha-NH$_2$) |
| --- | --- | --- |
| Example 1 | 7.5 g (13.3 mmole) | 7.4 g (12.9 mmole) 97% yield; 98.8 A % pure |
| Example 2 | 6.53 g (1 ⅙ mmole) | 6.4 g (11.1 mmole) 96% yield; 98.47 A % pure |

EXAMPLE 4

Preparation of CBZ-PipBu-N(Et)Gly-(L)-Asp(OBzl)-(L)-Cha-NH$_2$ (Step 4 of Scheme II)

A suspension of~equimolar amounts of TFA.N(Et)Gly-(L)-Asp(OBzl)-(L)-Cha-NH$_2$, CBZ-PipBu, and TBTU in EtOAc, DMF, and water (100:8:4 v/v, ~11: 1 total v/wt vs. TFA.N(Et)Gly-(L)-Asp(OBzl)-(L)-Cha-NH$_2$) are prepared. This suspension is cooled to 0–10° C. and about 3–4 equivalents of NMM is added. This mixture is allowed to warm to room temperature and stirred until HPLC indicates complete reaction (1–3 hours; solution occurs during this time). Water is added (2–3×original amount of water added) and the phases allowed to separate. The aqueous phase is reserved and the organic phase washed with two more portions of water. These combined aqueous washes are back-extracted with EtOAc, and the combined organic phases washed with 25% aqueous sodium chloride. The organic phase is concentrated under reduced pressure to~½ volume, and MTBE (~½ v:v vs. solution volume) added. This mixture is allowed to crystallize (several hours), and the solids are collected by filtration, rinsing with a chilled mixture of EtOAc and MTBE. The solids are dried under reduced pressure. The content of CBZ-PipBu-N(Et)Gly-(L)-Asp(OBzl)-(L)-Cha-NH$_2$ is analyzed by HPLC wt/wt assay. Yield is generally >80%, purity >95A %.

As a specific example of the above preparation, when the general procedure of Step 4 is followed, 7.25 g of TFA.N (Et)Gly-(L)-Asp(OBzl)-(L)-Cha-NH$_2$ provides 7.9 g of CBZ-PipBu-N(Et)Gly-(L)-Asp(OBzl)-(L)-Cha-NH$_2$ (>99A % pure, 0.08A % diastereomer at Asp), an 84% theoretical yield.

Elemental Analysis C$_{41}$H$_{57}$N$_5$O$_8$: H, N, C, 65.84, fd, 65.38; Mas Spec: M$_{calc}$ 747; M+1$_{obsvd}$$^{748}$; mp 101.6 (DSC); $^1$H NMR (δ vs TMS, CDCl$_3$): 0.88 m (1H); 0.98, m (1H); 1.13 (2H); 1.23, m (6H); 1.4, m (1H); 1.62–1.76, m (8H); 1.86, qd (1H); 2.35, t (1H); 2.74, dd (2H); 3.25, dd (1H); 3.47, q (2H); 3.7, d (1H) 3.84, d (1H); 4.15, ds (2H); 4.5, qd (1H); 4.68, dt (1H); 5.07, d (1H); 5.14 bd (2H); 5.16, d (1H); 7.28–7.39, m (10H); 7.57, dd (1H); $^{13}$C NMR (δ vs TMS, CDCl$_3$): [salient peaks] 66.93 (both benzyl carbons), 127.78–128.64 (both phenyl rings), 155.249, 170.00, 170.24, 171.69, 174.27, 175.21 (all carbonyl carbons).

EXAMPLE 5

Preparation of Hygroscopic Crystalline Form of N-[N-[N-(4-piperdin-4-yl)butanoyl)-N-ethylglycyl]-(L)-aspartyl]-(L)-β-cyclohexylalanine amide (Step 5 of Scheme II)

A mixture of CBZ-PipBu-N(Et)Gly-(L)-Asp(OBzl)-(L)-Cha-NH$_2$, ammonium formate, and 10% Pd/C in 20:1 alcohol/water (10:1 v/wt vs. CBZ-PipBu-N(Et)Gly-(L)-Asp(OBzl)-(L)-Cha-N H$_2$) is prepared. This mixture is heated to 40–50° C., and stirred until HPLC indicates complete reaction (1–2 hours). The mixture is cooled to room temperature and filtered to remove the catalyst. The resulting solution is heated to 40–50° C. and acetone added (~equal volume vs. filtered solution), allowing the solution to cool to 35–40° C. Seeds of N-[N-[N-(4-piperdin-4-yl)butanoyl)-N-ethylglycyl]-(L)-aspartyl]-(L)-β-cyclohexylalanine amide are added to the mixture and hygroscopic form of N-[N-[N-(4-piperdin-4-yl)butanoyl)-N-ethylglycyl]-(L)-aspartyl]-(L)-β-cyclohexyl-alanine amide crystallizes therefrom while cooling to room temperature (several hours). The solids are collected by filtration under a blanket of nitrogen, rinsing with acetone. The solids are dried under reduced pressure and analyzed for content of the hygroscopic crystalline form of N-[N-[N-(4-piperdin-4-yl)butanoyl)-N-ethylglycyl]-(L)-aspartyl]-(L)-β-cyclohcxylalanine amide (HPLC wt/wt assay). Yield is generally >85%, purity >95A %.

As a specific example of the above preparation, when the general procedure of Step 5 is followed, 5 g of CBZ-PipBu-N(Et)Gly-(L)-Asp(OBzl)-(L)-Cha-NH$_2$ provides 3.1 g of a hygroscopic crystalline form of N-[N-[N-(4-piperdin-4-yl) butanoyl)-N-ethylglycyl]-(L)-aspartyl]-(L)-β-cyclohexylalanine amide as a white solid (99.6A % pure), a stoichiometric yield of 89.4%.

Other compounds prepared according to the above Examples 1–5, but using the appropriate starting materials, include the following:

N-[N-[N-(4-(piperidin-4-yl)butanoyl)-N-ethylglycyl] aspartyl]valine,

N-[N-[N-(4-(piperidin-4-yl)butanoyl)-N-ethylglycyl] aspartyl]-D-valine,

N-[N-[N-(3-(piperidin-4-yl)propanoyl)-N-ethylglycyl] aspartyl]valine,

N-[N-[N-(5-(piperidin-4-yl)pentanoyl)-N-ethylglycyl] aspartyl]valine,

N-[N-[N-(4-(piperidin-4-yl)butanoyl)-N-ethylglycyl] aspartyl]-L-a-cyclohexyl glycine, N-[N-[N-(4-(piperidin-4-yl)butanoyl)-N-ethylglycyl] aspartyl]norleucine, N-[N-[N-(4-(piperidin-4-yl)butanoyl)-N-ethylglycyl] aspartyl]-L-α-(2,2-dimethyl)prop-3-yl glycine, N-[N-[N-(4-(piperidin-4-yl)butanoyl)-N-ethylglycyl] aspartyl]-L-β-decahydronaphth-1-yl alanine, N-[N-[N-(4-(piperidin-4-yl)butanoyl)-N-ethylglycyl] aspartyl]-L-α-(2-cyclohexylethyl)glycine, N-[N-[N-(4-(piperidin-4-yl)butanoyl)-N-ethylglycyl] aspartyl]phenylalanine, N-[N-[N-(4-(piperidin-4-yl)butanoyl)-N-ethylglycyl] aspartyl]-L-β-naphth-1-yl alanine, N-[N-[N-(4-(piperidin-4-yl)butanoyl)-N-ethylglycyl] aspartyl]-L-β-naphth-2-yl alanine, N-[N-[N-(4-(piperidin-4-yl)butanoyl)-N-ethylglycyl] aspartyl]-L-β-cyclohexyl alanine, ethyl ester, N-[N-[N-(4-(piperldin-4-yl)butanoyl)-N-ethylglycyl] aspartyl]-L-β-cis-decahydronaphth-2-ylalanine, N-[N-[N-(4-(piperidin-4-yl)butanoyl)-N-ethylglycyl] aspartyl]-α-aminocyclohexanecarboxylic acid, N-[N-[N-(4-(piperidin-4-yl)butanoyl)-N-ethylglycyl] aspartyl]-β-cyclohexyl-D-alanine, N-[N-[N-(4-(piperidin-4-yl)butanoyl)-N-ethylglycyl] aspartyl]-β-decahydronaphth-1-ylalanine, N-[N-[N-(4-(piperldin-4-yl)butanoyl)-N-ethylglycyl] aspartyl]-β-cyclohexylalanine ethyl amide, N-[N-[N-(4-(piperidin-4-yl)butanoyl)-N-ethylglycyl] aspartyl]-β-cyclooctylalanine, N-[N-[N-(4-(piperidin-4-yl)butanoyl)-N-ethylglycyl] aspartyl]-β-cyclohexylmethylalanine amide, N-[N-[N-(4-(piperidin-4-yl)butanoyl)-N-ethylglycyl] aspartyl]-β-adamant-1-ylalanine, N-[N-[N-(4-(piperidin-4-yl)butanoyl)-N-ethylglycyl] aspartyl]-β-(1,2,3,4)-tetrahydronaphth-5-ylalanine, N-[N-[N-(4-(piperldin-4-yl)butanoyl)-N-ethylglycyl] aspartyl]-β-(4-cyclohexyl)cyclohexylalanine, N-[N-[N-(4-(piperidin-4-yl)butanoyl)-N-ethylglycyl] aspartyl]-β-cycloheptylalanine, N-[N-[N-(4-(piperidin-4-yl)butanoyl)-N-ethylglycyl] aspartyl]-β-cyclooctylalanine amide, N-[N-[N-(4-(piperldin-4-yl)butanoyl)-N-ethylglycyl] aspartyl]-α-cyclohexylpropylglycine, N-[N-[N-(4-(piperidin-4-yl)butanoyl)-N-ethylglycyl] aspartyl]-β-cyclooctylmethylalanine, N-[N-[N-(4-(piperidin-4-yl)butanoyl)-N-ethylglycyl] aspartyl]-β-cyclopentylalanine, and N-[N-[N-(4-(piperidin-4-yl)butanoyl)-N-ethylglycyl] aspartyl]-β-cyclohexylmethylalanine ethyl ester, and

EXAMPLE 6

Preparation of 4-N-CBZ-Piperidone

A mixture of 40 Kg N-benzyloxycarbonyloxy) succinimide and 26 Kg (175 mol) 4-piperidone.HCl.H$_2$O in 38.8 Kg water and 88 Kg THF is stirred at 15° C.±5° C. until dissolution is (~15 minutes). NMM (22.8 Kg) is added to the agitated mixture (exothermic) while maintaining temperature at or below 20° C. The batch is agitated at 20° C.±5° C. for 2.5 hours, at which point HPLC indicated complete reaction. The mixture is diluted with 115.2 Kg MTBE and 38.8 Kg of water and agitated at 20° C.±5° C. for 5 minutes. Agitation is stopped, the layers are allowed to separate, and the aqueous (lower) layer is removed and discarded. The organic layer is washed with 2×129.6 Kg of water (agitate 5 minutes, separate phases, remove/discard aqueous [lower] phase). The organic layer is washed with 5.2 Kg of NaCl in 46.8 Kg of water (agitate 5 minutes, separate phases, remove/discard aqueous [lower] layer). The organic layer is treated with 11.5 Kg MgSO$_4$, with agitation for 1 hour, then the mixture is filtered. The reactor is rinsed with 8 Kg MTBE (filtered, combined with main filtrate; total filtrate water content: 0.52%).

The mixture volume is reduced by half via distillation at reduced pressure at 30° C. Vacuum is broken to nitrogen and the residue is cooled to 20° C. (pot residue water content: 0.43%). The residue is diluted with 57.6 Kg MTBE, then mixture volume is reduced again by half via distillation under vacuum at 30° C.

Vacuum is released to nitrogen and the mixture is cooled to 20° C. (pot residue water content: 0.25%). This is repeated 5 additional times. The final pot residue is diluted with 28.8 Kg of MTBE and mixed for 5 minutes, then assayed for water content and content of 4-N-CBZ-piperidone (water: 0.05%; wt/wt assay 4-N-CBZ-piperidone: 22.66 wt %, 35.36 kg, 155 mole, 88.6% stoich. yld.)

EXAMPLE 7

Preparation of PipBu

Under a N$_2$ purge and with agitation is prepared a solution of 53.5 Kg 3-carboxypropyl triphenylphosphomium bromide in 230.1 Kg of 1,2-dimethoxy-ethane. Potassium-tert-butoxide/THF (20 wt %, 141.8 Kg of soln.) is added over 35 minutes while maintaining the temperature at 24–28° C. The mixture is stirred at this temperature for 0.5 hour, at which point HPLC indicates a complete reaction. The agitated mixture is cooled to 10° C.±2° C., then to the mixture is added 96.45 Kg (Titer: 1.15 m 4-CBZ-piperidone in MTBE over 40 minutes such that batch temperature remains at 12° C.±2° C. The mixture is agitated at this temperature for 10 minutes, then is heated to 20° C.±2° C. and agitated at that temperature for 2 hours. To the agitated mixture is added a solution of 22.5 Kg concentrated aq. HCl in 245.6 Kg of water so as to maintain the mixture at 20° C.±2° C.; the final pH is 0.5. The mixture is extracte with agitation, with 214.0 Kg methyl-tert-butyl ether. Agitation is stopped, the phases are allowed to separate, and the aqueous layer (lower) is removed and discarded. The organic phase is washed with 133.75 Kg of water (agitate 5 minutes, separate, remove/discard aqueous [lower] layer), then with 10.7 Kg 50% NaOH in 126.8 Kg water (agitate 10 minutes, separate layers, removed/discard organic [upper] layer). The aqueous layer is extracted with 2×123.05 Kg EtOAc (agitate 5 minutes, separate layers, remove/discard organic [upper] layers). To the agitated aqueous layer is added 13.1 Kg concentrated aq. HCl to a pH of 2.5–3.5 (final: 2.82), then the mixture is extracted with 123.05 Kg EtOAc (agitate 5 minutes, separate layers, remove/discard aqueous [lower] layer). The EtOAc solution is washed with 133.75 Kg water (agitate 5 minutes, separate layers, remove/discard aqueous [lower] layer), then is assayed (wt/wt) for content of CBZ-PipBuen (total wt.: 194.86 kg, 17.05% CBZ-PipBuen [33.22 kg, 108 mole], 87.9% stoich yld.).

The EtOAc solution of PipBuen, along with 6.6 Kg 5% Pd/C (50% water by wt.) is charged with agitation to a stainless steel pressure tank, then the mixture is heated to 55° C.±2° C. Potassium formate (38.2 Kg) dissolved in 66.4 Kg of water is added such that the reaction mixture temperature remains at 55° C.±2° C. (~30 minutes). The mixture is agitated at 55° C.±2° C. for 2 hours at which time reaction was complete (HPLC). To the reactor is added 6.6 Kg celite and 33.2 Kg water, the mixture agitated, then filtered. The reactor is rinsed with 33.2 Kg of water (filtered, added to main filtrate). The filtrate is placed in a new vessel, cooled to 20–25° C., the layers allowed to separate, and the organic layer removed and discarded. The aqueous layer is acidified with 52.1 Kg of concentrated aq. HCl to pH 2–3 (final: 2.82), then extracted with 4×129.5 Kg methylene chloride (agitate 5 minutes, separate layers, remove/discard organic [lower] layers). The aqueous phase is adjusted to pH 6.1 by addition, with agitation, of 17.85 Kg 50% aq. NaOH. The mixture is filtered to afford a 224 Kg solution containing 17.6 Kg (103 mole) of 4-(3'-carboxypropyl)piperidine.

EXAMPLE 8

Preparation of CBZ-PipBu

The 224 Kg solution of 4-(3'-carboxypropyl)piperidine in aq., NaOH is combined with 55.3 Kg THF and the mixture cools with agitation to 8° C. +2° C. NMM (20.9 Kg) is added while maintaining temperature at <10° C. After addition is complete, the temperature is adjusted to 8° C. +2° C., then 25.7 Kg of 1-(benzyloxocarbonyl)succinimide dissolved in 49.8 Kg in THF is added over Ihour, while maintaining the temperature at <15° C. The reaction is complete (analytical HPLC) after 3 hours at 10–15° C. Concentrate aq. HCl (29.9 Kg) is added to adjust the pH to 2.5–3.5 (final: 3.3), then 61.4 Kg MTBE is added and the mixture is agitated for 5 minutes. Agitation is stopped, the layers allowed to separate, and the aqueous (lower) layer is separated (waste). The MTBE layer is washed with three 83.1 Kg portions of water (10 minute, then 5 minute and 5 minute agitation periods); the aqueous phase is allowed separate and removed (waste) in each case. A solution of 8.3 Kg of 50% aq. NaOHl in 95.7 Kg water is added without agitation, then upon complete addition, the mixture is agitated for~5 minutes. Agitation is stopped, the phases are allowed to separate, and the organic (upper) layer is separated and discarded. The aqueous layer is returned to the reactor and extracted with 2×38.4 Kg of methyl-tert-butyl ether (agitated 5 minutes, layers separated, organic [upper] layers removed/discarded). This operation is repeated using 18.5 Kg methyl-tert-butyl ether. The aqueous layer, returned to the reactor, is acidified to pH 2.5–3.5 (final: 3.37) with 9.9 Kg of concentrated aq. HCl. The mixture is extracted with 76.4 Kg methyl-tert-butyl ether (agitate 5 minutes, separate layers, lower [aqueous] layer removed/discarded). The organic layer is washed (5 minute agitation) with a solution of 1.1 Kg NaHCO$_3$ in 12.4 Kg of water (agitate 5 minutes, separate layers, aqueous layer [lower] removed/discarded), then with 41.5 Kg of water (agitate 5 minutes, separate layers, aqueous layer [lower]

removed/discarded). The reactor is placed under reduced pressure and volatile solvents removed at 55° C. until distillate flow ceases. Toluene (32.4 Kg) is added, and the mixture is distilled under atmospheric pressure until distillate flow stopped, while the batch temperature climbs to 90–95° C. The mixture is then cooled to 30–35° C., heptane (56.85 Kg) is charged to the reactor (two phases), the mixture is heated to 90–95° C. (single phase), then recooled to 38–42° C. Seed crystals of CBZ-PipBu are added, and the product crystallizes from the mixture over a 1hour period. The solid is collected by filtration and washed with 19.35 Kg of 1:2 toluene/heptane, then with 33.4 Kg heptane. The filter cake is dried under vacuum at 40° C. (to 0.13% loss on drying analysis) to afford 22.4 Kg (72.96 mole, 42% stoich. yid from 4-piperidone) of CBZ-PipBu.

EXAMPLE 9

Preparation of CBZ-PipBuen

To a suspension of 82 g of 3-carboxypropyl triphenylphosphonium bromide in 407 mL 1,2-diethoxyethane at 14° C. is added over 25 minutes 220 g of 20 wt % potassium tert-butoxide in tetrahydrofuran while maintaining the reaction mixture temperature at 24–28° C. The mixture is stirred for 1 hour, cooled to 10° C., then a solution of 52.5 g of 4-N-CBZ-piperidone in 246 mL of tert-butyl methyl ether is added over 30 minutes. while maintaining cooling. After addition is complete, the mixture is stirred at 12° C. for 10 minutes, then warmed to 20° C. and stirred for an additional 30 minutes. The reaction mixture is treated with 410 mL 1 N aq. HCl for 10 minutes, diluted with 328 mL oft-butyl methyl ether, and then the phases are separated. The organic phase is washed with 205 mL of water, then 210 mL of 1 N aq. NaOH. The NaOH layer, which contains the product, is collected separately, washed with three 189 g portions of ethyl acetate, acidified to pH 3.48 with concentrated HCl, then extracted with 189 mL of ethyl acetate. The ethyl acetate layer is separated, washed with 211 mL of water, then dried for 30 minutes over 10 g of $MgSO_4$, filtered, and concentrated in vacuo. The oily residue (50.7 g) is crystallized from toluene/heptane to afford a total of 29.46 g (50.9% yield; 95A % pure) of CBZ-PipBuen.

Mass Spec: $M^{calc}$. 303, $M+1_{obsvd}$ 304; $^1H$ NMR: (δ vs TMS, $CDCl_3$) 2.2, t (2H); 2.25, t (2H); 2.35, m (4H); 3.45, m (4H); 5.15, s (2H); 5.2, m (1H); 7.33, 2(5H). $^{13}C$ NMR (δ vs TMS, $CDCl_3$) 22.43, 28.2, 34.26, 35.66, 44.88, 45.74, 67.20, 122.02, 127.83, 127.95, 128.45, 128.69, 128.90. 136.17, 136.72, 155.34, 178.39

EXAMPLE 10

Preparation of CBZ-PipBuen-N(Et)Gly-(L)-Asp(OBzl)-(L)-Cha-$NH_2$ (Alternate Step 4 of Scheme II)

CBZ-PipBuen (70 g, 0.23 mole) and DMF (230 mL) are added to a 1 L jacketed flask and stirred with cooling to 0° C., then TBTU (74.9 g, 0.23 mole) is added add at once. The temperature is maintained at 0° C. and the addition of DIPEA (61.9 g, 0.61 mole) is started. After 45 min., TFA-N(Et)Gly-(L)-Asp(OBzl)-(L)-Cha-$NH_2$ (138.7 g, 0.24 mole) is added as a solution in DMF (230 mL). The pH is adjusted to 7–8 by addition of DIPEA (45 mL) and the mixture allowed to reach ambient temperature. After 2 hours, reaction is complete (HPLC analysis). The mixture is quenched into water (2.5 L) and extracted with EtOAc (1 L). The aqueous phase is back-extracted with EtOAc (0.3 L).

The organic layers are combined, washed with aqueous citric acid (5% w/w, 2×1 L), washed with aqueous $NaHCO_3$ (5% w/w, 2×1 L), and washed with water (2 L) crystallization. The solids are collected by suction on a Buchner funnel, washed with EtOAc/Heptane (2:1 v/v, 1 L) and dried to constant weight to yield CBZ-PipBuen-N(Et)Gly-(L)-Asp(OBzl)-(L)-Cha-$NH_2$ (143.2 g, 0.19 mole, 83% yield).

Elemental analysis: $C_{41}H_{55}N_5O_7$ C: calc. 66.02; fd, 65.53, H, N. Mass Spec: $M_{calc}$ 745.91; $M+1_{obsvd}$ 746.

$^1H$ NMR (δ vs TMS, $CDCl_3$): 0.86 qd (1H); 0.98, qd (1H); 1.16, t (2H), 1.24, dt (6H); 1.37, m (1H); 1.64–1.78, m (4H); 1.86, qd (1H); 2.2 bd (4H); 2.35, m (4H); 2.4, m (2H); 2.74, dd (1H); 3.07, m (4H); 3.52, d, (1H); 3.85, d (1H); 4.12, q (1IH); 4.49, qd (1H); 4.68, dt (1H); 5.07, d (1H); 5.14, s (1H); 5.16, d (1H); 5.22, t (2H); 6.45, s (1H); 7.28, d (1H); 7.26, s (5H); 7.35, s (5H); 7.56, d (1H).

$^{13}C$ NMR (δ vs TMS, $CDCl_3$): 14.15, 22.68, 24.95, 25.61, 26.03, 26.45, 28.20, 31.71, 32,89, 33.80, 33.89, 34.00, 35.63, 38.37, 44.79, 45.13, 45.65, 50.23, 51.34, 60.40, 66.87, 67.06, 76.50, 77.13, 77.77, 122.46, 126.88, 127.80–128.60, 135.15, 155.19, 170.11, 170.20, 171.61, 173.76, 175.35.

EXAMPLE 11

Preparation of Hygroscopic Crystalline Form of N-[N-[N-(4-Piperdin-4-yl)butanoyl)-N-ethylglycyl]-(L)-aspartyl]-(L)-β-cyclohexylalanine Amide (Alternate Step 5 of Scheme II)

CBZ-PipBuen-N(Et)Gly-(L)-Asp(OBzl)-(L)-Cha-$NH_2$ (140 g, 0.19 mole), ammonium formate (61 g, 0.96 mole) and 10% Pd/C (50% wet, degussa type, 28 g) are added to a 5 L jacketed flask. EtOH (200 proof, 1260 mL), iPrOH (70 mL) and water (DI, 70 g) are added. This mixture is heated to 40–50° C., and stirred until HPLC indicates complete reaction (5 hours). The mixture is cooled to room temperature and filtered to remove the catalyst. The resulting solution is heated to 40–50° C. and acetone (~equal volume vs. filtered solution) added, allowing the solution to cool to 35–40° C. Seeds of N-[N-[N-(4-piperdin-4-yl)butanoyl)-N-ethylglycyl]-(L)-aspartyl]-(L)-β-cyclohexylalanine amide are added to the mixture and hygroscopic form of N-[N-[N-(4-piperdin-4-yl)butanoyl)-N-ethylglycyl]-(L)-aspartyl]-(L)-β-cyclohexylalanine amide crystallizes therefrom while cooling to room temperature (several hours). The solids are collected by suction on a Buchner funnel under a blanket of nitrogen, the cake is washed with acetone and air dried to constant weight to yield N-[N-[N-(4-piperdin-4-yl) butanoyl)-N-ethylglycyl]-(L)-aspartyl]-(L)-β-cyclohexylalanine amide (84.3 g, 0.16 mole, 84.8% yield, >95A %).

EXAMPLE 12

Concatenated Preparation of TFA-N(Et)Gly-(L)-Asp(OBzl)-(L)Cha-$NH_2$ (Alternate of Steps 1–3 of Scheme II)

A 500 mL flask fitted with a temperature probe is charged with BOC-N(Et)-Gly (20.3 g, 0.1 mole). N-hydroxysuccinimide (11.5 g, 0.1 mole) and dichloromethane (200 mL). The mixture is stirred at moderate speed and to the resulting solution is added DCC (20.6 g, 0.1 mole) in one portion as a solid. This solution is stirred for 1 hour during which a small exotherm is noticed (temperature rise from 20° C. to 28° C.) and DCU precipitates. The resulting suspension is vacuum filtered using a Buchner funnel equipped with a Whatman #1 filter paper. The cake is washed with dichloromethane (2×25 mL). The filtrates are returned to the original 500 mL flask and then (L)Asp(OBzl) (22.3 g, 0.1 mole), NMM (33.8 mL, 0.3 mole) and DMF (80 g, 1.01 mole) are added successively. After being stirred for 2 hours at room temperature, formation of BOC-N(Et)Gly-(L)-Asp(OBzl) is complete (HPLC monitoring). The reaction mixture is poured into an extraction funnel containing ice water (100 mL). The mixture is acidified with HCl (36%, 25 mL) until pH 1. The layers are split and the dichloromethane layer is washed with ice water (100 mL) and the phases split (aq. phase pH 3–4). The dichloromethane layer is returned to the original 500 mL flask which is charged successively with $NH_2$-(L)-Cha-$NH_2$ (17 g, 0.1 mole)), N-hydroxysuccinimide (11.5 g, 0.1 mole) and DCC (20.6 g, 0.1 mole) in one portion each as solids. After stirring for 2 hours at room temperature, the formation of BOC-N(Et)Gly-(L)-Asp(OBzl)-(L)-Cha-$NH_2$ is complete (HPLC monitoring) and the DCU is vacuum filtered using a Buchner funnel equipped with a Whatman #1 filter paper. The cake is washed with dichloromethane (2×25 mL). The filtrate is transferred to an extraction funnel and washed with deionized water (200 mL) containing N-methyl morpholine (15 mL, pH 8–9). The phases are split and the dichloromethane layer is again washed with water (DI, 2×150 mL). The dichloromethane phase is washed with 150 mL of 1 N HCl (pH 1). The phases are split and the dichloromethane layer is washed with deionized water (200 mL, pH 3). The dichloromethane solution of BOC-N(Et)Gly-(L)-Asp(OBzl)-(L)-Cha-$NH_2$ is returned to a clean 500 mL flask and then charged with TFA (100 mL). After being stirred for 2 hours at room temperature, the formation of TFA.HN(Et)Gly-(L)-Asp(OBzl)-(L)-Cha-$NH_2$ is complete (HPLC monitoring). The reaction mixture is distilled under vacuum to remove the dichloromethane and most of the TFA, then MTBE (500 mL) and seeds are added to effect product crystallization. The mixture is vacuum filtered using a Buchner funnel equipped with a Whatman #1 filter paper. The cake is washed with MTBE (2×25 mL) and air-dried to afford TFA.HN(Et)Gly-(L)-Asp(OBzl)-(L)-Cha-$NH_2$ (46.8 g, 81.5% yield) as a white solid (>97A % pure, <0.2A % D-Asp diast.).

EXAMPLE 13

Preparation of Stable Non-hygroscopic Crystalline Form of N-[N-[N-(4-Piperdin-4-yl)butanoyl)-N-ethylglycyl]-(L)-aspartyl]-(L)-β-cyclohexylalanine Amide Method A. Static Conversion Hygroscopic crystalline form of N-[N-[N-(4-piperdin-4-yl)butanoyl)-N-ethylglycyl]-(L)-aspartyl]-(L)-β-cyclohexylalanine amide (7.45 Kg) is milled in a hammer mill. The resulting solid, 7.35 kg, is placed in a stainless steel dryer tray (90×28 cm) and the tray is covered with perforated aluminum foil. The tray is then sealed into a humidity oven (LUNAIRE Humidity Cabinet model no. CEO 941 W-3); the oven is kept sealed throughout the form conversion process except to remove samples for analysis. The oven is adjusted to 40% RH and 60° C. and kept at those levels for 1 hour. The humidity oven is then adjusted to 80% RH/60° C. and held at those levels for 12 hours. A sample is removed after 18 hours at 80% RH/60° C. and checked by X-Ray powder diffraction analysis to assess the conversion to the non-hygroscopic crystalline form of N-[N-[N-(4-piperdin-4-yl)butanoyl)-N-ethylNlycyl]-(L)-aspartyl]-(L)-β-cyclohexylalanine amide. The humidity oven is resealed and adjusted to 40% RH/60° C. and held there for 2 hours. The oven is readjusted to ambient conditions, then the tray is then removed from the oven and the non-hygroscopic crystalline form of N-[N-[N-(4-piperdin-4-yl)butanoyl)-N-ethylglycyl]-(L)-aspartyl]-(L)-β-cyclohexylalanine amide is yielded (7.2 kg, 96.6% yield). Confirmation of the conversion is determined by an X-Ray powder diffraction graph (FIG. 1). The X-ray powder diffraction is also tabularized as a function of increasing order of the angle of diffraction (2θ) corresponding to the interplanar distance of the crystal (d) in angstrom units (Å), counts per second (Cps) and relative peak intensity (%) (Table 1).

TABLE 1

| N | 2θ | d | Cps | % |
|---|-----|------|------|------|
| 1 | 5.065 | 17.4314 | 86.00 | 5.82 |
| 2 | 6.323 | 13.9672 | 248.00 | 6.78 |
| 3 | 7.518 | 11.7489 | 221.00 | 14.95 |
| 4 | 8.163 | 10.8222 | 496.00 | 33.56 |
| 5 | 8.780 | 10.0633 | 155.00 | 10.49 |
| 6 | 10.383 | 8.5125 | 218.00 | 14.75 |
| 7 | 11.35 | 7.7886 | 112.00 | 7.58 |
| 8 | 12.596 | 7.0218 | 999.00 | 67.59 |
| 9 | 3.858 | 6.3852 | 316.00 | 21.38 |
| 10 | 15.191 | 5.8274 | 1338.00 | 90.53 |
| 11 | 16.476 | 5.3759 | 481.00 | 32.54 |
| 12 | 16.745 | 5.2901 | 556.00 | 37.62 |
| 13 | 17.980 | 4.9294 | 679.00 | 45.95 |
| 14 | 18.572 | 4.7735 | 1079.00 | 73.00 |
| 15 | 18.799 | 4.7165 | 1230.00 | 83.22 |
| 16 | 19.147 | 4.6315 | 1229.00 | 83.15 |
| 17 | 19.619 | 4.5211 | 1380.00 | 93.37 |
| 18 | 20.200 | 4.3924 | 1246.00 | 84.30 |
| 19 | 20.466 | 4.3360 | 1478.00 | 100.00 |
| 20 | 20.870 | 4.2528 | 1088.00 | 73.61 |
| 21 | 21.625 | 4.1061 | 584.00 | 39.51 |
| 22 | 22.088 | 4.0210 | 891.00 | 60.28 |
| 23 | 22.840 | 3.8903 | 613.00 | 41.47 |
| 24 | 23.947 | 3.7129 | 597.00 | 40.39 |
| 25 | 24.569 | 3.6203 | 680.00 | 46.01 |
| 26 | 25.608 | 3.4757 | 506.00 | 34.24 |
| 27 | 27.015 | 3.2978 | 1100.00 | 74.42 |
| 28 | 27.837 | 3.2022 | 420.00 | 28.42 |
| 29 | 27.967 | 3.1877 | 400.00 | 27.06 |
| 30 | 29.255 | 3.0502 | 536.00 | 36.27 |
| 31 | 29.689 | 3.0066 | 603.00 | 40.80 |
| 32 | 30.665 | 2.9130 | 518.00 | 35.05 |
| 33 | 31.318 | 2.8538 | 451.00 | 30.51 |
| 34 | 31.894 | 2.8036 | 533.00 | 36.06 |
| 35 | 33.370 | 2.6829 | 518.00 | 35.05 |
| 36 | 33.562 | 2.6679 | 552.00 | 37.35 |
| 37 | 33.919 | 2.6407 | 581.00 | 39.31 |
| 38 | 34.840 | 2.5730 | 561.00 | 37.96 |
| 39 | 35.789 | 2.5069 | 559.00 | 37.82 |
| 40 | 35.940 | 2.4967 | 560.00 | 37.89 |
| 41 | 36.780 | 2.4416 | 740.00 | 50.07 |
| 42 | 37.042 | 2.4249 | 736.00 | 49.80 |
| 43 | 37.959 | 2.3684 | 683.00 | 46.21 |
| 44 | 39.017 | 2.3066 | 643.00 | 43.50 |

Method B. Dynamic Conditions a. Form Conversion

Figure 2:
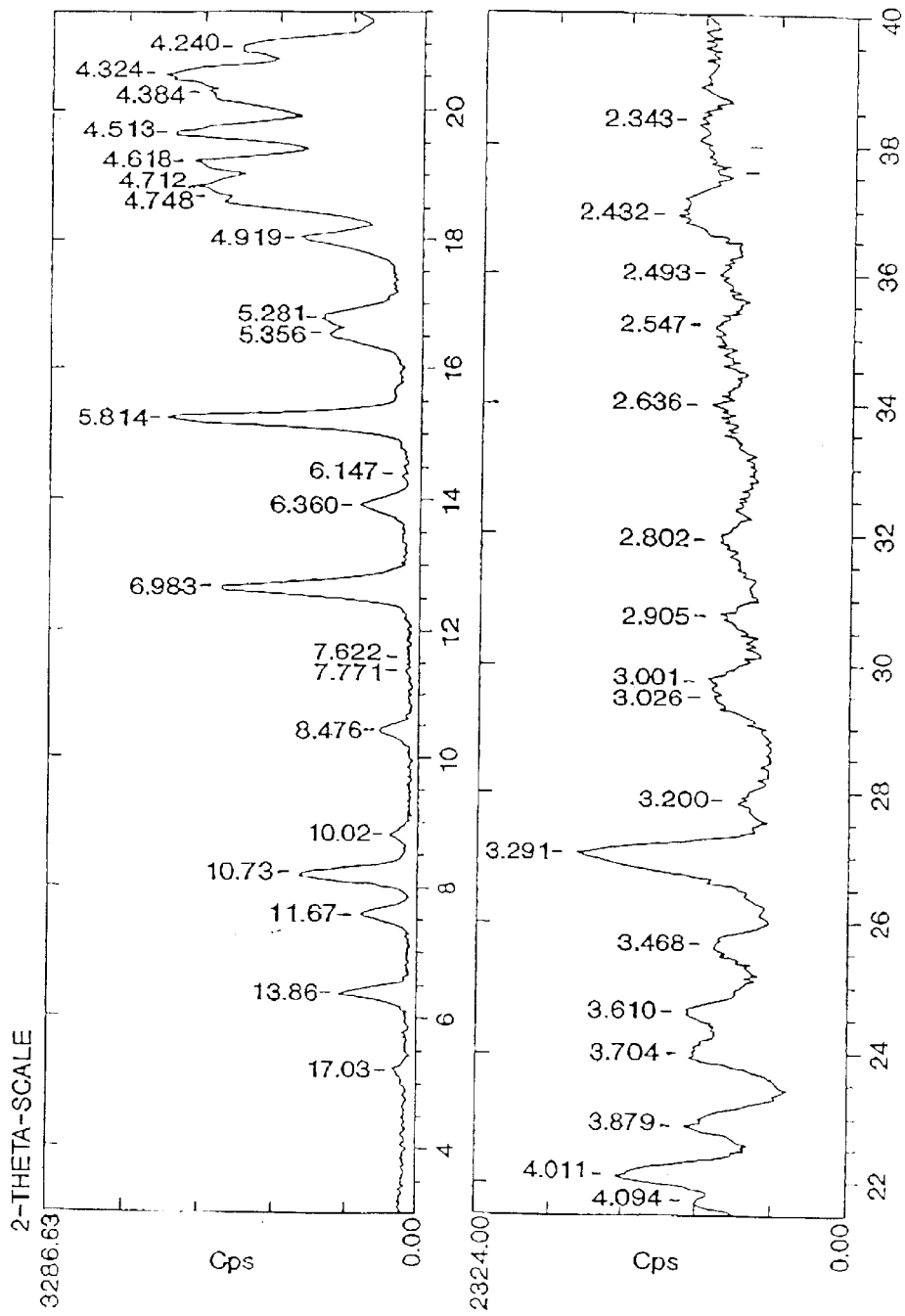
FIG. 2 represents a x-ray powder diffraction graph of a sample of the non-hygroscopic crystalline form of N-[N-[N-(4-piperdin-4-yl)butanoyl)-N-ethylglycyl]-(L)-aspartyl]-(L)-β-cyclohexylaianine amide prepared in Example 13, Method B (a).

Hygroscopic crystalline form of N-[N-[N-(4-piperdin-4-yl)butanoyl)-N-ethylglycyl]-(L)-aspartyl]-(L)-β-cyclohexylalanine amide (50 g) is placed in a 400 mL graduated cylinder (bed height 6 cm) on a ring stand equipped with a mechanical stirrer. The apparatus is place in a humidity-controlled oven (oven (LUNAIRE Humidity Cabinet model no. CEO 941 W-3). Agitation is set at 275 rpm, and the temperature and RH are adjusted over 30 minutes to 60° C. and 40%, respectively. The compound is held at these conditions for 1 hour, then conditions are changed over 45 minutes to 80% RH/60° C. The compound is then held at these conditions for 16 hours before the oven is reset to 40% RH/60° C. and held there for 3.25 hours. The compound is then allowed to return to ambient conditions (bed height 4 cm), then removed from the cylinder to yield the non-hygroscopic crystalline form of N-[N-[N-(4-piperdin-4-yl)butanoyl)-N-eyhylglycyl]-(L)-aspartyl]-(L)-

β-cyclohexylalanine amide (yield >95%). Confirmation of the conversion is determined by X-Ray powder diffraction analysis (FIG. 2). The X-ray powder diffraction is also tabularized as a function of increasing order of the angle of diffraction (2θ) corresponding to the interplanar distance of the crystal (d) in angstrom units (Å), counts per second (Cps) and relative peak intensity (%) (Table 2).

TABLE 2

| N | 2θ | d | Cps | % |
|---|---|---|---|---|
| 1 | 5.186 | 17.0268 | 196.00 | 8.43 |
| 2 | 6.371 | 13.8615 | 722.00 | 31.07 |
| 3 | 7.570 | 11.6689 | 516.00 | 22.20 |
| 4 | 8.232 | 10.7323 | 1094.00 | 47.07 |
| 5 | 8.817 | 10.0206 | 257.00 | 11.06 |
| 6 | 10.428 | 8.4761 | 365.00 | 15.71 |
| 7 | 11.377 | 7.7714 | 129.00 | 5.55 |
| 8 | 11.600 | 7.6223 | 117.00 | 5.55 |
| 9 | 12.667 | 6.9828 | 1805.00 | 77.67 |
| 10 | 13.913 | 6.3599 | 551.00 | 23.71 |
| 11 | 14.398 | 6.1468 | 178.00 | 7.66 |
| 12 | 15.226 | 5.844 | 2285.00 | 98.32 |
| 13 | 16.538 | 5.3557 | 861.00 | 37.05 |
| 14 | 16.773 | 5.2814 | 929.00 | 39.97 |
| 15 | 18.019 | 4.9190 | 1132.00 | 48.71 |
| 16 | 18.672 | 4.7483 | 1871.00 | 80.51 |
| 17 | 18.815 | 4.7125 | 2052.00 | 88.30 |
| 18 | 19.204 | 4.6178 | 2071.00 | 89.11 |
| 19 | 19.654 | 4.5132 | 2226.00 | 95.78 |
| 20 | 20.237 | 4.3845 | 1939.00 | 83.43 |
| 21 | 20.523 | 4.3240 | 2324.00 | 100.00 |
| 22 | 20.934 | 4.2400 | 1656.00 | 71.26 |
| 23 | 21.691 | 4.0938 | 923.00 | 39.72 |
| 24 | 22.143 | 4.0112 | 1411.00 | 60.71 |
| 25 | 22.910 | 3.8786 | 994.00 | 42.77 |
| 26 | 24.007 | 3.7037 | 964.00 | 41.48 |
| 27 | 24.642 | 3.6097 | 991.00 | 42.64 |
| 28 | 25.642 | 3.6097 | 991.00 | 42.64 |
| 29 | 27.070 | 3.2913 | 1687.00 | 72.59 |
| 30 | 27.855 | 3.2002 | 688.00 | 29.60 |
| 31 | 29.497 | 3.0258 | 843.00 | 36.27 |
| 32 | 29.497 | 3.0013 | 878.00 | 37.78 |
| 33 | 30.751 | 2.9051 | 809.00 | 34.81 |
| 34 | 31.916 | 2.8017 | 821.00 | 35.33 |
| 35 | 33.982 | 2.6360 | 882.00 | 37.95 |
| 36 | 35.200 | 2.5475 | 865.00 | 37.22 |
| 37 | 36.001 | 2.4926 | 841.00 | 36.19 |
| 38 | 36.927 | 2.4322 | 1106.00 | 47.59 |
| 39 | 38.389 | 2.3429 | 968.00 | 41.65 | b. Form Conversion

Figure 3:
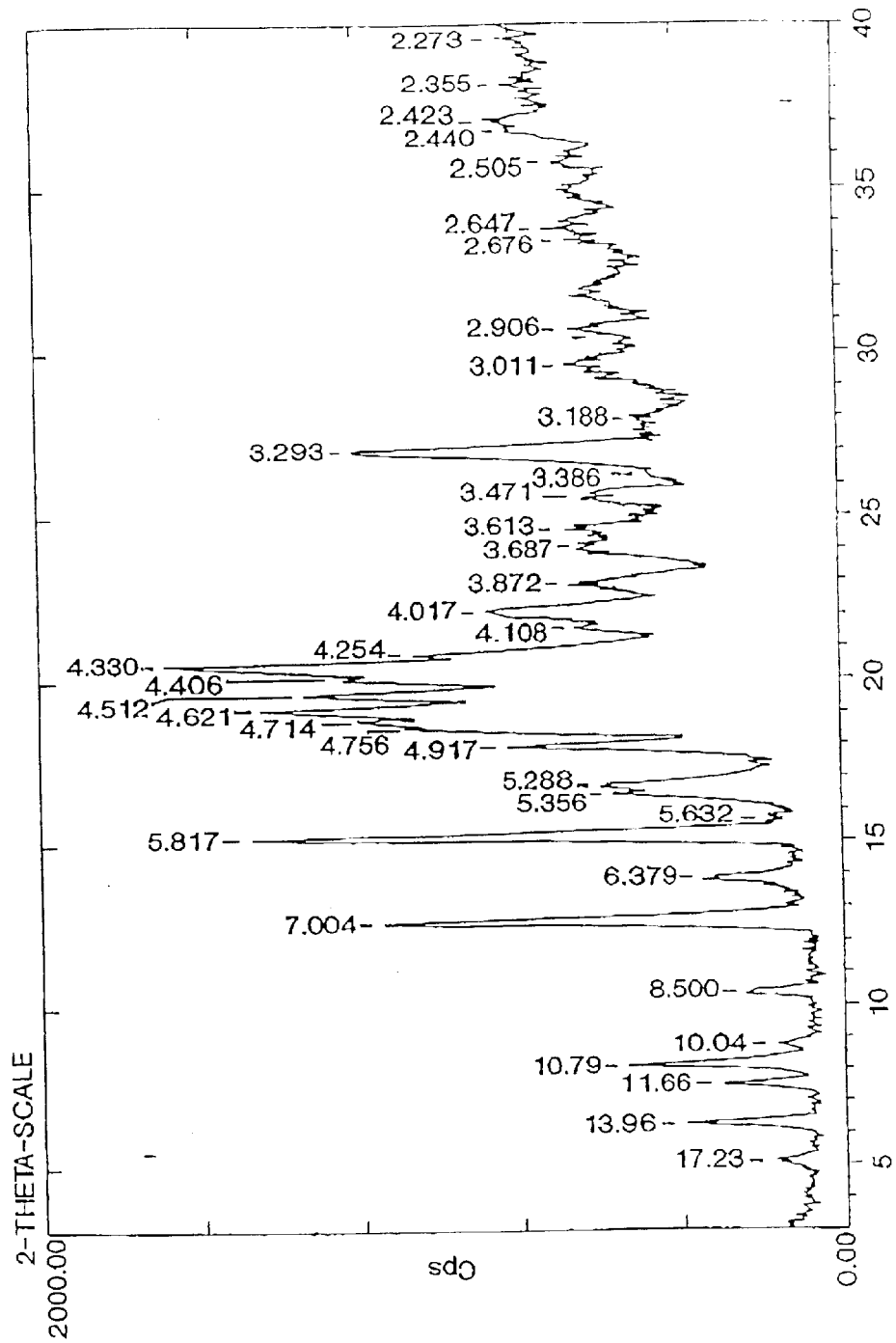
FIG. 3 represents a x-ray powder diffraction graph of a sample of the non-hygroscopic crystalline form of N-[N-[N-(4-piperdin-4-yl)butanoyl)-N-ethylglycyl]-(L)-aspartyl]-(L)-β-cyclohexylalanine amide prepared in Example 13, Method B (b).

Hygroscopic crystalline form of N-[N-N(4-piperdin-4-yl)butanoyl)-N-ethylglycyl]-(L)-aspartyl]-(L)-β-cyclohexylalanine amide (370 g) is charged into a 2 L rotary evaporator flask. The flask is placed on the rotary evaporator (Heidolph UV 2002) and lowered into a preheated (58° C.) bath (Heidolph MR 2002). The apparatus is placed under a vacuum of 60 mBar using a vacuum pump (Divatrion DV1), then vacuum is broken in a controlled fashion to admit a humid atmosphere created in a separate, heated, water-containing flask. The admission of humid atmosphere is controlled by a humidity controlling apparatus (Vausalo Humiditique and Temperature Traumettor) so as to achieve a RH of 79% within the apparatus (130–180 mBar internal pressure). The rotary evaporator vessel is then rotated at 145–160 revolutions per minute over a period of 5 hours while the heating bath is maintained at 60° C. and the RH maintained within the vessel at 71–79%. Vacuum is then broken to nitrogen, the vessel and its contents allowed to cool to ambient temperature, and the product is removed to yield the non-hygroscopic crystalline form of N-[N-[N-(4-piperdin-4-yl)butanoyl)-N-ethylglycyl]-(L)-aspartyl]-(L)-β-cyclohexyl-alanine amide. A second 317 lot of roscopic crystal line form of N-[N-[N-(4-piperdin-4-yl)butanoyl)-N-ethylglycyl]-(L)-aspartyl]-(L)-β-cyclohexyl-alanine amide is similarly treated to provide the non-hygroscopic crystalline form of N-[N-[N-(4-piperdin-4-yl)butanoyl)-N-ethylglycyl]-(L)-aspartyl]-(L)-β-cyclohexyl-alanine amide. Confirmation of the conversion is determined by X-Ray powder diffraction analysis (FIG. 3). The two lots together afforded 667 g of the non-hygroscopic crystalline form of N-[N-[N-(4-piperdin-4-yl)butanoyl)-N-ethylglycyl]-(L)-aspartyl]-(L)-β-cyclohexyl-alanine amide (97% yield overall). Confirmation of the conversion is determined by X-Ray powder diffraction analysis (FIG. 3). The X-ray powder diffraction is also tabularized as a funtion of increasing order of the angle of diffraction (2θ) corresponding to the interplanar distance of the crystal (d) in angstrom units (Å), counts per second (Cps) and relative peak intensity (%) (Table 3).

TABLE 3

| N | 2θ | d | Cps | % |
|---|---|---|---|---|
| 1 | 5.124 | 17.2309 | 180.00 | 10.17 |
| 2 | 6.328 | 13.9565 | 408.00 | 23.05 |
| 3 | 7.574 | 11.6623 | 305.00 | 17.23 |
| 4 | 8.191 | 10.7851 | 556.00 | 31.41 |
| 5 | 8.797 | 10.0432 | 166.00 | 9.38 |
| 6 | 10.398 | 8.5004 | 244.00 | 13.79 |
| 7 | 12.628 | 7.0040 | 1198.00 | 67.68 |
| 8 | 13.871 | 6.3791 | 353.00 | 19.94 |
| 9 | 15.218 | 5.8172 | 1543.00 | 87.18 |
| 10 | 15.723 | 5.6317 | 187.00 | 10.56 |
| 11 | 16.538 | 5.3558 | 589.00 | 33.28 |
| 12 | 16.751 | 5.2882 | 621.00 | 35.08 |
| 13 | 18.024 | 4.9175 | 869.00 | 49.10 |
| 14 | 18.640 | 4.7563 | 1156.00 | 65.31 |
| 15 | 18.809 | 4.7141 | 1241.00 | 70.11 |
| 16 | 19.191 | 4.6210 | 1521.00 | 85.93 |
| 17 | 19.659 | 4.5120 | 1413.00 | 79.83 |
| 18 | 20.865 | 4.4064 | 1303.00 | 73.62 |
| 19 | 20.495 | 4.3299 | 1770.00 | 100.00 |
| 20 | 20.865 | 4.2539 | 1120.00 | 63.28 |
| 21 | 21.616 | 4.1077 | 683.00 | 38.59 |
| 22 | 22.113 | 4.0166 | 919.00 | 51.92 |
| 23 | 22.950 | 3.8719 | 697.00 | 39.38 |
| 24 | 24.117 | 3.6871 | 659.00 | 37.23 |
| 25 | 24.618 | 3.6132 | 716.00 | 40.45 |
| 26 | 25.644 | 3.4709 | 662.00 | 37.40 |
| 27 | 26.297 | 3.3862 | 486.00 | 27.46 |
| 28 | 27.052 | 3.2934 | 1270.00 | 71.75 |
| 29 | 27.960 | 3.1885 | 518.00 | 29.27 |
| 30 | 29.640 | 3.0115 | 705./00 | 39.38 |
| 31 | 30.744 | 2.9058 | 695.00 | 39.27 |
| 32 | 33.465 | 2.6755 | 697.00 | 39.38 |
| 33 | 33.840 | 2.6467 | 764.00 | 43.16 |
| 34 | 35.812 | 2.5053 | 736.00 | 41.58 |
| 35 | 36.811 | 2.4396 | 858.00 | 48.47 |
| 36 | 37.076 | 2.4228 | 919.00 | 51.92 |
| 37 | 38.185 | 2.3549 | 870 | 49.15 |
| 38 | 39.622 | 2.2728 | 882.00 | 49.83 |

EXAMPLE 14

Figure 4:
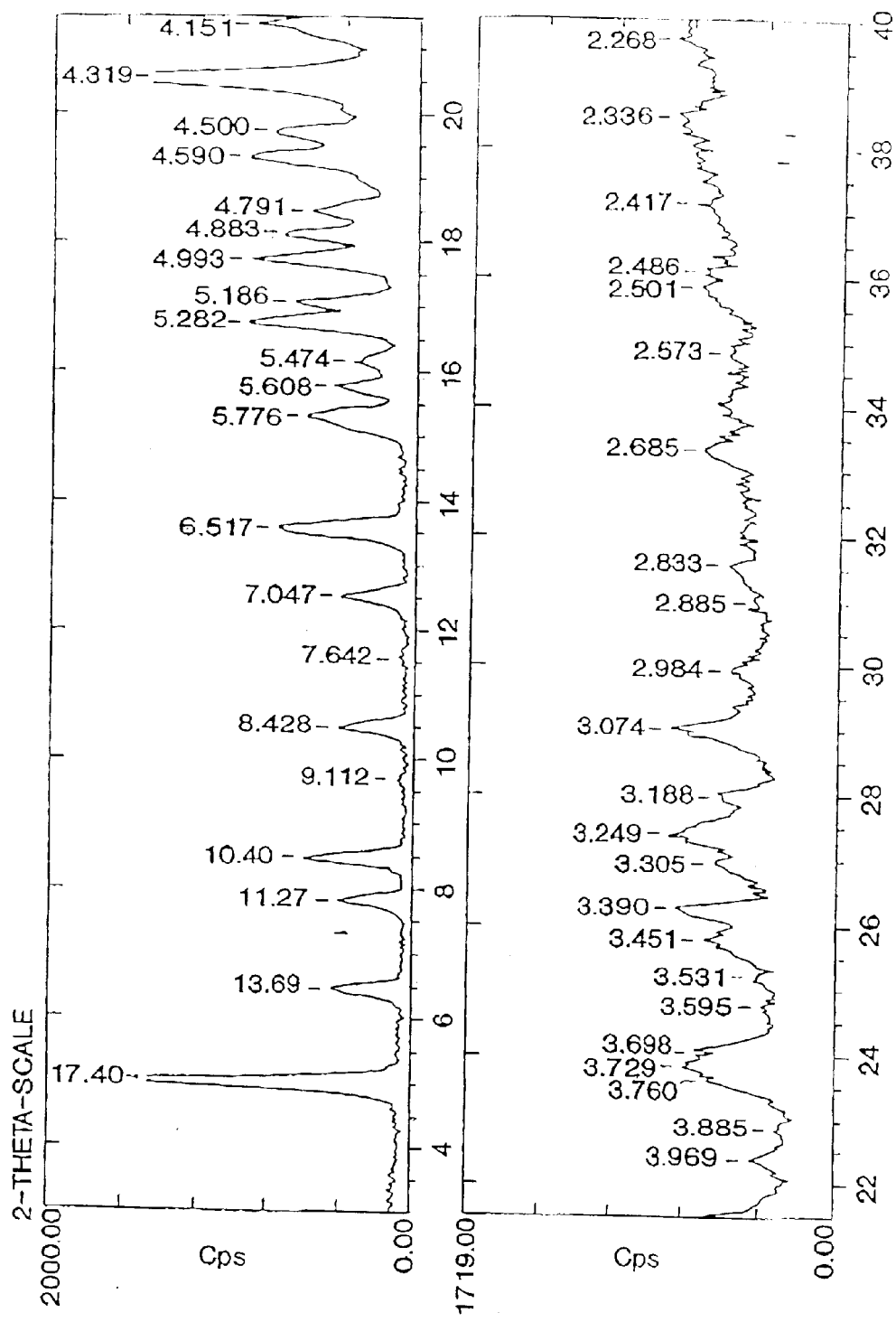
FIG. 4 represents a x-ray powder diffraction graph of a sample of the hygroscopic crystalline form of N-[N-[N-(4-piperdin-4-yl)butanoyl)-N-ethylglycyl]-(L)-aspartyl]-(L)-β-cyclohexylalanine amide prepared as in noted in Example 14.
Figure 5:
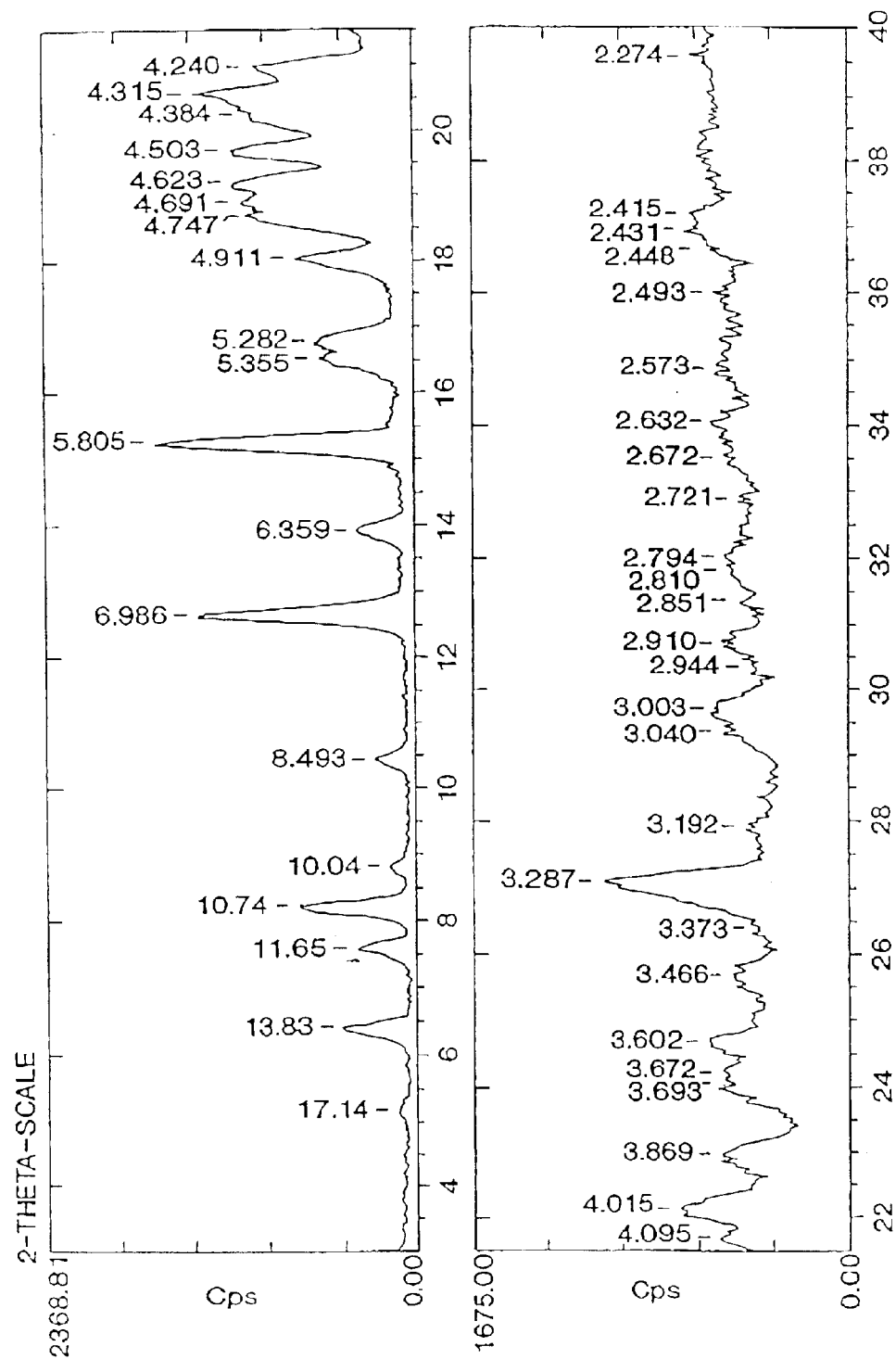
FIG. 5 represents a x-ray powder diffraction graph of a sample of the non-hygroscopic crystalline form of N-[N-[N-(4-piperdin-4-yl)butanoyl)-N-ethylglycyl]-(L)-aspartyl]-(L)-β-cyclohexylalanine amide prepared as in noted in Example 14.

X-ray Powder Diffraction Graphs of A Sample of N-[N-[N-(4-Piperdin-4-yl)butanoyl)-N-ethylglycyl]-(L)-aspartyl]-(L)-β-cyclohexylalanine Amide in its Hygroscopic Crystalline Form and Its Converted Non-hygroscopic Crystalline Form A sample of hygroscopic crystalline N-[N-[N-(4-piperdin-4-yl)butanoyl)-N-ethylglycyl]-(L)-aspartyl]-(L)-β-cyclohexylalanine amide is prepared as in Example 5 or 11, and converted to the corresponding non-hygroscopic crystalline form according to a method of Example 13. The x-ray powder diffraction graphs of the hygroscopic crystalline form and non-hygroscopic crystalline form are shown respectively in FIGS. 4 and 5. The X-ray powder diffraction graphs for the hygroscopic crystalline form and non-hygroscopic crystalline form are also tabularized as a function of increasing order of the angle of diffraction (2θ) corresponding to the interplanar distance of the crystal (d) in angstrom units (Å), counts per second (Cps) and relative peak intensity (%) in Table 4 and Table 5, respectively.

TABLE 4

| N | 2θ | d | Cps | % |
|---|---|---|---|---|
| 1 | 5.073 | 17.4037 | 1487.00 | 86.50 |
| 2 | 6.451 | 13.6905 | 447.00 | 26.00 |
| 3 | 7.837 | 11.2712 | 411.00 | 23.91 |
| 4 | 8.491 | 10.4049 | 602.00 | 35.02 |
| 5 | 9.699 | 9.1119 | 93.00 | 5.41 |
| 6 | 10.488 | 8.4278 | 421.00 | 24.49 |
| 7 | 11.570 | 7.6423 | 92.00 | 5.35 |
| 8 | 12.550 | 7.0474 | 411.00 | 23.91 |
| 9 | 13.576 | 6.5168 | 760.00 | 44.21 |
| 10 | 15.327 | 5.7763 | 606.00 | 35.25 |
| 11 | 15.790 | 5.6080 | 456.00 | 26.53 |
| 12 | 16.179 | 5.4739 | 346.00 | 20.13 |
| 13 | 16.770 | 5.2824 | 938.00 | 54.57 |
| 14 | 17.085 | 5.1856 | 685.00 | 39.85 |
| 15 | 17.750 | 4.9927 | 924.00 | 53.75 |
| 16 | 18.151 | 4.8835 | 741.00 | 43.11 |
| 17 | 18.504 | 4.7909 | 593.00 | 34.50 |
| 18 | 19.323 | 4.5897 | 930.00 | 54.10 |
| 19 | 19.714 | 4.4996 | 792.00 | 46.07 |
| 20 | 20.545 | 4.3194 | 1719.00 | 100.00 |
| 21 | 21.388 | 4.1510 | 897.00 | 52.18 |
| 22 | 22.381 | 3.9691 | 373.00 | 21.70 |
| 23 | 22.870 | 3.8852 | 258.00 | 15.01 |
| 24 | 23.640 | 3.7604 | 563.00 | 32.75 |
| 25 | 23.841 | 3.7292 | 680.00 | 39.56 |
| 26 | 24.048 | 3.6976 | 623.00 | 36.24 |
| 27 | 24.746 | 3.5949 | 338.00 | 19.66 |
| 28 | 25.200 | 3.5311 | 366.00 | 21.29 |
| 29 | 25.792 | 3.4513 | 590.00 | 34.32 |
| 30 | 26.266 | 3.3901 | 731.00 | 42.52 |
| 31 | 26.959 | 3.3045 | 555.00 | 32.29 |
| 32 | 27.426 | 3.2494 | 769.00 | 44.74 |
| 33 | 27.967 | 3.1876 | 528.00 | 30.72 |
| 34 | 29.020 | 3.0744 | 771.00 | 44.85 |
| 35 | 29.922 | 2.9837 | 491.00 | 28.56 |
| 36 | 30.970 | 2.8851 | 384.00 | 22.34 |
| 37 | 31.552 | 2.8332 | 510.00 | 29.67 |
| 38 | 33.338 | 2.6854 | 627.00 | 36.47 |
| 39 | 34.838 | 2.5731 | 520.00 | 30.25 |
| 40 | 35.873 | 2.5012 | 653.00 | 37.99 |
| 41 | 36.107 | 2.4855 | 639.00 | 37.17 |
| 42 | 37.162 | 2.4174 | 683.00 | 39.73 |
| 43 | 38.509 | 2.3359 | 775.00 | 45.08 |
| 44 | 39.701 | 2.2684 | 784.00 | 45.61 |

TABLE 5

| N | 2θ | d | Cps | % |
|---|---|---|---|---|
| 1 | 5.152 | 17.1371 | 123.00 | 7.34 |
| 2 | 6.386 | 13.8287 | 483.00 | 28.84 |
| 3 | 7.580 | 11.6540 | 389.00 | 23.22 |
| 4 | 8.225 | 10.7410 | 752.00 | 44.90 |
| 5 | 8.801 | 10.0390 | 180.00 | 10.75 |
| 6 | 10.408 | 8.4928 | 276.00 | 16.48 |
| 7 | 12.660 | 6.9863 | 1399.00 | 83.52 |
| 8 | 13.914 | 6.3594 | 391.00 | 23.34 |
| 9 | 15.251 | 5.8047 | 1675.00 | 100.00 |
| 10 | 16.541 | 5.3548 | 608.00 | 36.30 |
| 11 | 16.771 | 5.2818 | 652.00 | 38.93 |
| 12 | 18.047 | 4.9112 | 775.00 | 46.27 |
| 13 | 18.676 | 4.7472 | 1078.00 | 64.36 |
| 14 | 18.902 | 4.6910 | 1099.00 | 65.61 |
| 15 | 19.182 | 4.6231 | 1151.00 | 68.72 |
| 16 | 19.697 | 4.5035 | 1164.00 | 69.49 |
| 17 | 20.240 | 4.3838 | 1049.00 | 62.63 |
| 18 | 20.568 | 4.3147 | 1403.00 | 83.76 |
| 19 | 29.933 | 4.2403 | 1024.00 | 61.13 |
| 20 | 21.684 | 4.0951 | 569.00 | 33.97 |
| 21 | 22.122 | 4.0150 | 746.00 | 44.54 |
| 22 | 22.970 | 3.8685 | 564.00 | 33.67 |

TABLE 5-continued

| N | 2θ | d | Cps | % |
|---|---|---|---|---|
| 23 | 24.080 | 3.6927 | 546.00 | 32.60 |
| 24 | 24.218 | 3.6720 | 556.00 | 33.19 |
| 25 | 24.694 | 3.6023 | 618.00 | 36.90 |
| 26 | 25.680 | 3.4662 | 510.00 | 30.45 |
| 27 | 26.400 | 3.3732 | 403.00 | 24.06 |
| 28 | 27.105 | 3.2871 | 1093.00 | 65.25 |
| 29 | 27.929 | 3.1920 | 450.00 | 26.87 |
| 30 | 29.360 | 3.0395 | 555.00 | 33.13 |
| 31 | 29.724 | 3.0031 | 595.00 | 35.52 |
| 32 | 30.340 | 2.9435 | 429.00 | 25.61 |
| 33 | 30.693 | 2.9105 | 552.00 | 32.96 |
| 34 | 31.353 | 2.8507 | 476.00 | 28.42 |
| 35 | 31.822 | 2.8098 | 531.00 | 31.70 |
| 36 | 32.006 | 2.7940 | 545.00 | 32.54 |
| 37 | 32.885 | 2.7213 | 485.00 | 28.96 |
| 38 | 33.508 | 2.6722 | 547.00 | 32.66 |
| 39 | 34.040 | 2.6316 | 606.00 | 36.18 |
| 40 | 34.839 | 2.5730 | 580.00 | 34.63 |
| 41 | 35.998 | 2.4928 | 596.00 | 35.58 |
| 42 | 36.680 | 2.4480 | 629.00 | 37.55 |
| 43 | 36.948 | 2.4309 | 727.00 | 43.40 |
| 44 | 37.197 | 2.4152 | 703.00 | 41.97 |
| 45 | 39.602 | 2.2739 | 697.00 | 41.61 |

EXAMPLE 15

Figure 6:
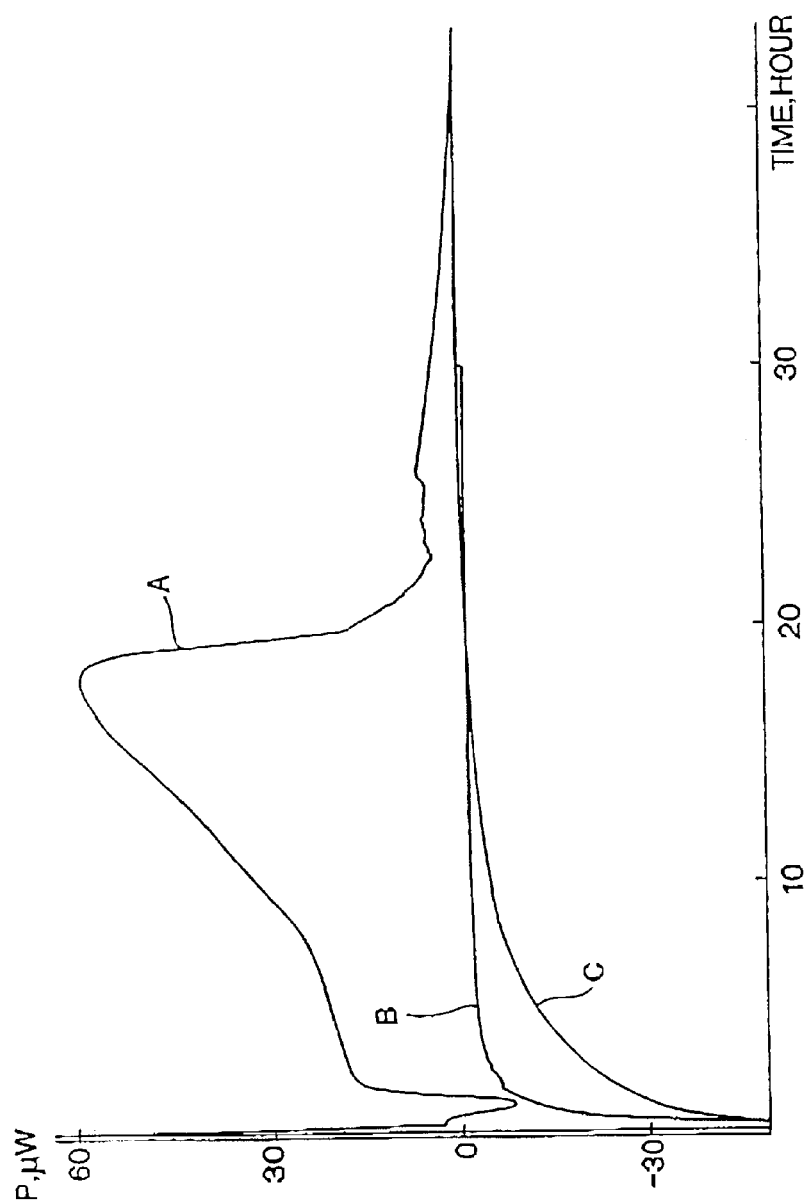
FIG. 6 represents isothermal microcalorimetric graph of the power output as a function of time for three different experiments which are undertaken as described in Experiment 15. The experiments monitor the thermal activity of different crystalline forms of N-[N-[N-(4-piperdin-4-yl)butanoyl)-N-ethylglycyl]-(L)-aspartyl]-(L)-β-cyclohexylalanine amide when exposed to various solvent vapors. The (A) trace in FIG. 6 shows that a strong exothermic event takes place when hygroscopic N-[N-[N-(4-piperdin-4-yl)butanoyl)-N-ethylglycyl]-(L)-aspartyl]-(L)-β-cyclohexylalanine amide prepared according to Examples 5 or 11 is exposed to 80% RH (saturated KCl solution) at 40° C. over 30 hours, during which exposure the hygroscopic form of the compound is converted to the non-hygroscopic form of the compound. The (B) trace in FIG. 6 shows no exothermic conversion event takes place when hygroscopic N-[N-[N-(4-piperdin-4-yl)butanoyl)-N-ethylglycyl]-(L)-aspartyl]-(L)-β-cyclohexylalanine amide prepared according to Examples 5 or 11 is exposed to methanol vapors at 40° C. (a solvent other than water in which the compound is soluble), and thus that methanol does not support mobility within the crystals of that form for the conversion to the non-hygroscopic form. The (C) trace in FIG. 6 shows no exothermic conversion event takes place when non-hygroscopic N-[N-[N-(4-piperdin-4-yl)butanoyl)-N-ethylglycyl]-(L)-aspartyl]-(L)-β-cyclohexylalanine amide prepared according to Example 13 is exposed to 40° C./80% RH, and thus that the non-hygroscopic form of the compound does not undergo a form conversion at those conditions, i.e., it is a stable form.
Figure 7:
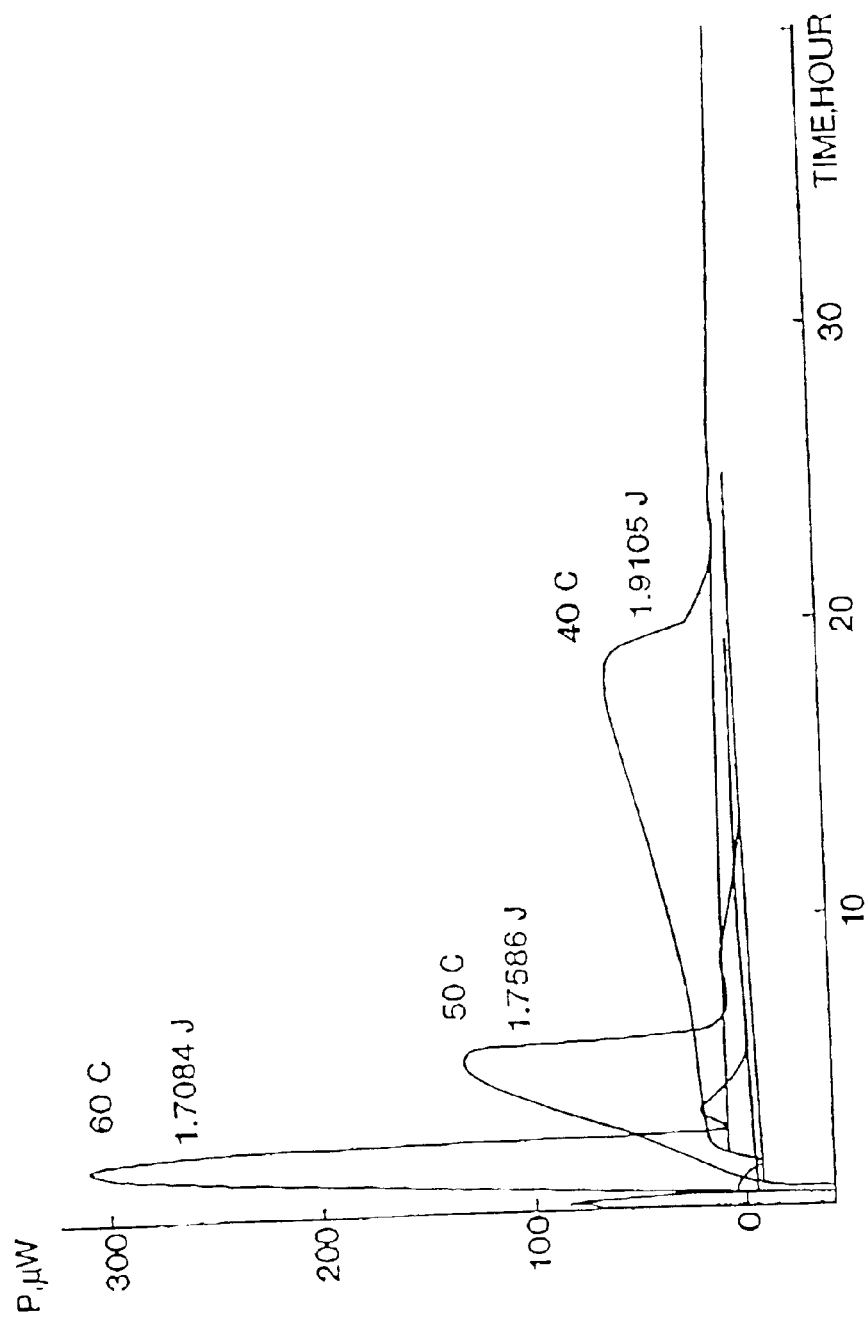
FIG. 7 represents isothermal microcalorimetric graph of the power output as a function of time for three different experiments which are undertaken as described in Experiment 15. The experiments monitor the thermal activity of the conversion of the hygroscopic crystalline form of N-[N-[N-(4-piperdin-4-yl)butanoyl)-N-ethylglycyl]-(L)-aspartyl]-(L)-β-cyclohexylalanine amide to its nonhygroscopic form when exposed to 80% RH at 40° C., 50° C. and 60° C. The Figure represents that the conversion takes approximately 24 hours at 40° C., 6.5 hours at 50° C. and 3 hours at 60° C.
Figure 8:
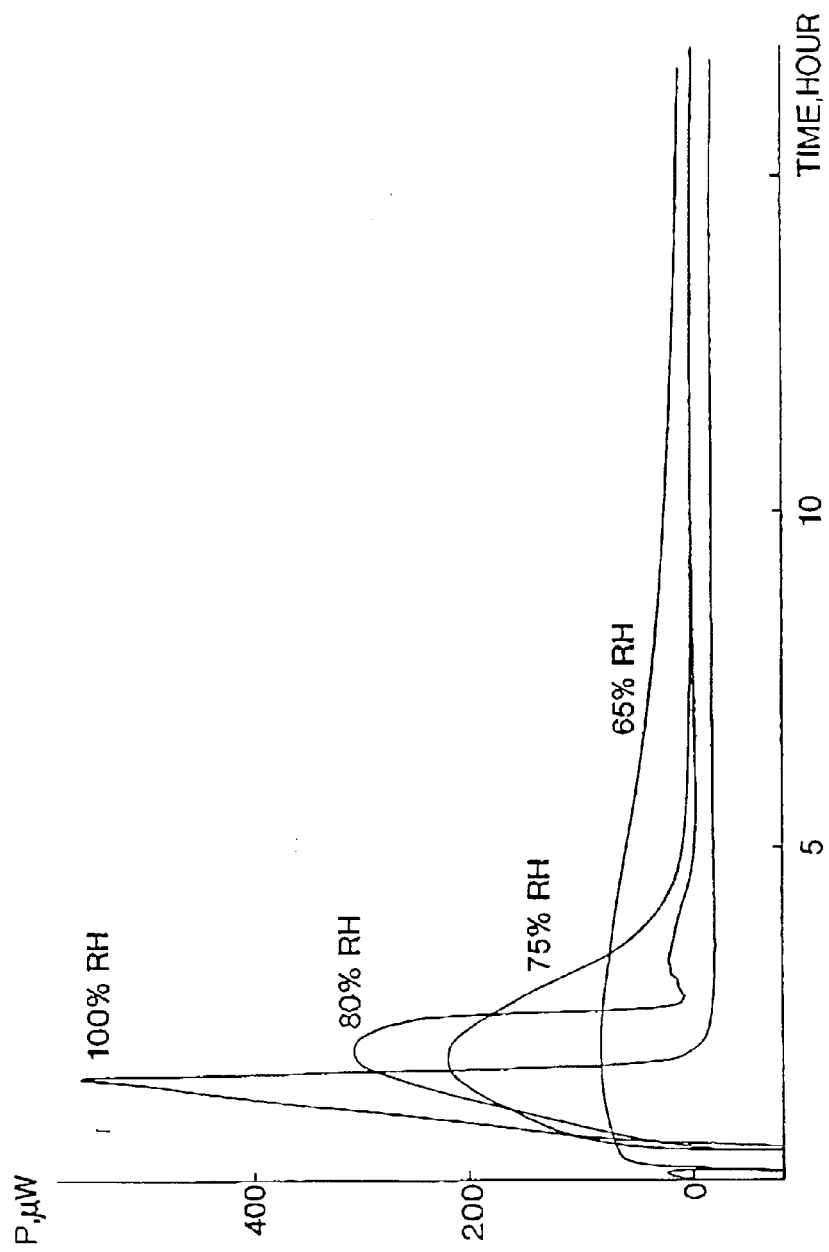
FIG. 8 represents isothermal microcalorimetric graph of the power output as a function of time for four different experiments which are undertaken as described in Experiment 15. The experiments monitor the thermal activity of the conversion of the hygroscopic crystalline form of N-[N-[N-(4-piperdin-4-yl)butanoyl)-N-ethylglycyl]-(L)-aspartyl]-(L)-β-cyclohexylalanine amide to its non-hygroscopic form when exposed at 60° C. to 65% RH, 75% RH, 80% RH and 100% RH. A salient features of FIG. 8 is that higher relative humidities produce a faster conversion. Another salient feature is that the conversion to the non-hygroscopic form of the compound occurs at 100% RH at 60° C. without the liquification which occurs to the hygroscopic form at room temperature. Based on these results it is expected that the rate of conversion to the non-hygroscopic form is much faster than the rate of liquification of hygroscopic form at 60° C.

Isothermal Microcalorimetric Experiments on Hygroscopic and Non-hygroscopic Crystalline Forms of N-[N-[N-(4-Piperdin-4-yl)butanoyl)-N-ethylglycyl]-(L)-aspartyl]-(L)-β-cyclohexylalanine Amide Isothermal microcalorimetry experiments on hygroscopic and non-hygroscopic crystalline forms of N-[N-[N-(4-piperdin-4-yl)butanoyl)-N-ethylglycyl]-(L)-aspartyl]-(L)-β-cyclohexylalanine amide are performed on a Thermometric® Thermal Activity Monitor (TAM). Solid state conversions of the different chrystalline forms are studied by exposing the forms to different humidities or solvent vapors at different temperatures. The saturated salt solutions used to obtain different humidities were: KCl (80% RH), NaCl (75% RH), and NaBr (65% RH). Approximately 100 mg quantities of the forms are weighed into a TAM glass ampule and a microhygrostate containing a saturated salt solution (with excess solid) or an organic solvent is placed inside the ampule. The ampule is sealed, equilibrated to the temperature of the experiment, and lowered into the measuring position in the TAM. An identical system containing washed sea sand, in place of the form subject to testing, is placed on the reference side. Output power (μW) is measured as a function of time (FIGS. 6–8).

EXAMPLE 16

Figure 9:
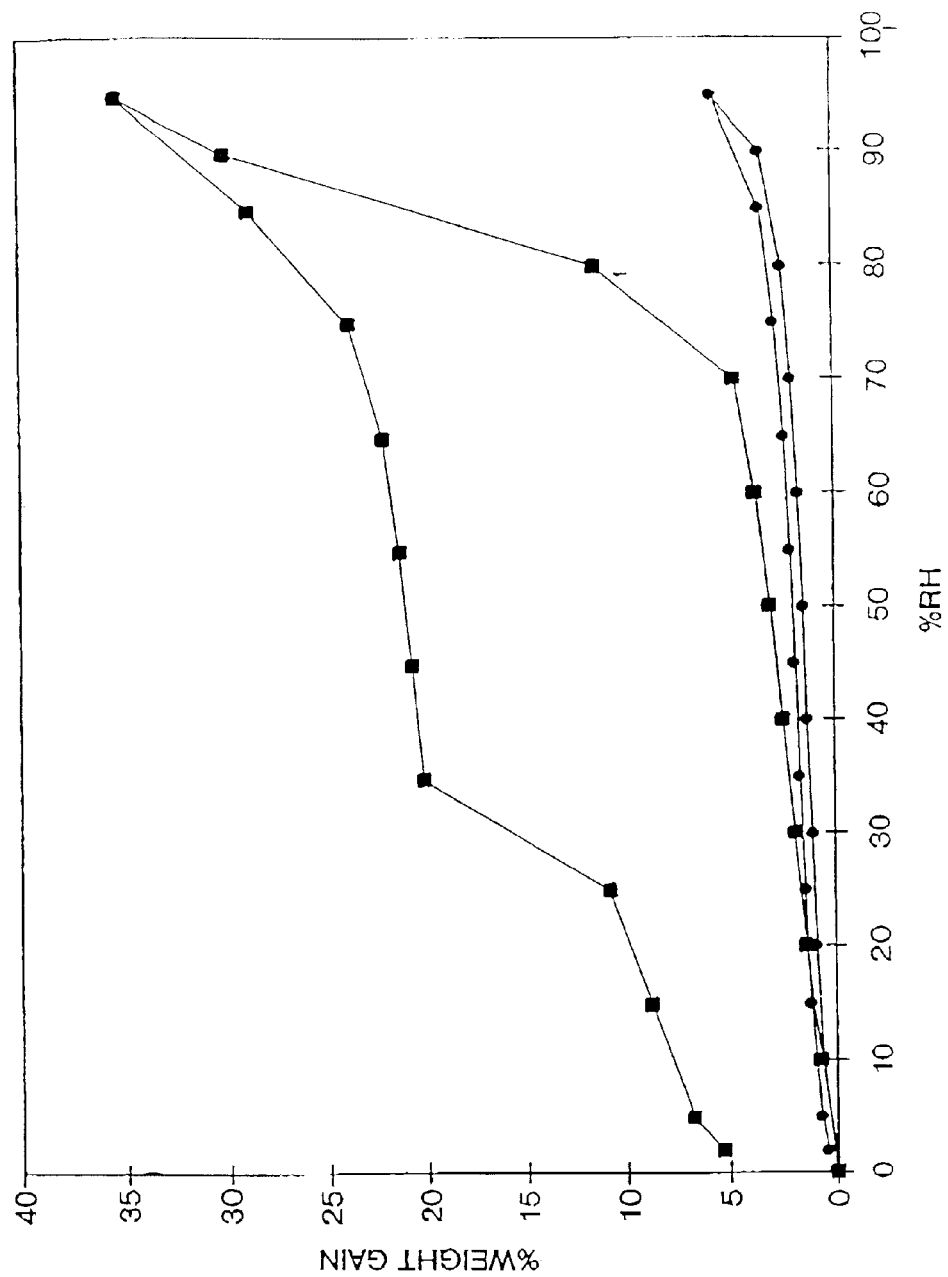
FIG. 9 represents a comparison of the % weight gain vs. % RH plots for the hygroscopic (|) and non-hygroscopic (•) forms of N-[N-[N-(4-piperdin-4-yl)butanoyl)-N-ethylglycyl]-(L)-aspartyl]-(L)-β-20 cyclohexylalanine amide at 25° C. which are undertaken as described in Experiment 16.

Moisture Sorption Isotherms of Hygroscopic and Non-hygroscopic Crystalline Forms of N-[N-[N-(4-Piperdin-4-yl)butanoyl)-N-ethylglycyl]-(L)-aspartyl]-(L)-β-cyclohexylalanine Amide Moisture Sorption Isotherms of hygroscopic and non-hygroscopic crystalline forms of N-[N-[N-(4-piperdin-4-yl)butanoyl)-N-ethylglycyl]-(L)-aspartyl]-(L)-β-cyclohexylalanine amide are obtained on a VTI MB300G moisture balance. The experiments are conducted either by subjecting approximately 15 mg of the subject crystalline form to increasing and decreasing steps of % RH and following the weight gain (at each equilibrium step) as a function of % RH (FIG. 9) or by holding the subject crystalline form at constant humidity and following the weight gain as a function of time.

The compound of formula II exhibits useful pharmacological activity and accordingly are incorporated into pharmaceutical compositions and used in the treatment of patients suffering from certain pathological conditions.

The present invention is also directed to a method for the treatment of a patient suffering from, or subject to, conditions which can be ameliorated or prevented by the administration of an inhibitor of platelet aggregation by inhibiting fibrinogen binding to activated platelets and other adhesive glycoproteins involved in platelet aggregation and blood clotting. Furthermore, the present invention is direct to a method for preventing or treating thrombosis associated with certain disease states, such as myocardial infarction, stroke, peripheral arterial disease and disseminated intravascular coagulation in humans and other mammals.

Reference herein to treatment should be understood to include prophylactic therapy as well as treatment of established conditions.

The present invention also includes within its scope a pharmaceutical composition which comprises a pharmaceutically acceptable amount of at least one compound of formula I in association with a pharmaceutically acceptable carrier or excipient.

In practice compounds or compositions for treating according to the present invention may administered by any suitable means, for example, by topically, inhalation, parenterally, rectally or orally, but they are preferably administered orally.

The compound of formula II may be presented in forms permitting administration by the most suitable route and the invention also relates to pharmaceutical compositions containing at least one compound according to the invention which are suitable for use in human or veterinary medicine. These compositions may be prepared according to conventional methods, using one or more pharmaceutically acceptable adjuvants or excipients. The adjuvants comprise, inter alia, diluents, sterile aqueous media and the various non-toxic organic solvents. The compositions may be presented in the form of tablets, pills, capsules, (granules, powders, aqueous solutions or suspensions, injectable solutions, elixirs, syrups and the like, and may contain one or more agents chosen from the group comprising sweeteners, flavorings, colorings, stabilizers or preservatives in order to obtain pharmaceutically acceptable preparations.

The choice of vehicle and the content of active substance in the vehicle are generally determined in accordance with the solubility and chemical properties of the product, the particular mode of administration and the provisions to be observed in pharmaceutical practice. For example, excipients such as lactose, sodium citrate, calcium carbonate. dicalcium phosphate and disintegrating agents such as starch, alginic acids and certain complex silica gels combined with lubricants such as magnesium stearate, sodium lauryl sulfate and talc may be used for preparing tablets. To prepare a capsule, it is advantageous to use lactose and high molecular weight polyethylene glycols. When aqueous suspensions are used they may contain emulsifying agents or agents which facilitate suspension. Diluents such as sucrose, ethanol, polyethylene glycol, propylene glycol, glycerol and chloroform or combinations thereof can beemployed as well as other materials.

For parenteral administration, emulsions, suspensions or solutions of the compounds according to the invention in vegetable oil, for example sesame oil, groundnut oil or olive oil, or aqueous-organic solutions such as water and propylene glycol, injectable organic esters such as ethyl oleate, as well as sterile aqueous solutions of the pharmaceutically acceptable salts, are used. The solutions of the salts of the products according to the invention are also useful for administration by intramuscular or subcutaneous injection. The aqueous solutions, also comprising solutions of the salts in pure distilled water, may be used for intravenous administration with the proviso that their pH is suitably adjusted, that they are judiciously buffered and rendered isotonic with a sufficient quantity of glucose or sodium chloride and that they are sterilized by heating, irradiation and/or microfiltration.

Topical administration, gels (water or alcohol based), creams or ointments containing compounds of the invention may be used. Compounds of the invention may be also incorporated in a gel or matrix base for application in a patch, which would allow a controlled release of compound through transdermal barrier.

Solid compositions for rectal administration include suppositories formulated in accordance with known methods and containing at least one compound of formula II.

The percentage of active ingredient in a composition according to the invention may be varied such that it should constitutes a proportion of a suitable dosage. Obviously, several unit dosage forms may be administered at about the same time. A dose employed may be determined by a physician or qualified medical professional, and depends upon the desired therapeutic effect, the route of administration and the duration of the treatment, and the condition of the patient. The dosage regimen in carrying out the method of this invention is that which insures maximum therapeutic response until improvement is obtained and thereafter the minimum effective level which gives relief. In general, the oral dose may be between about 0.1 mg/kg and about 100 mg/kg, preferably between about 0.1 mg/kg to 20 mg/kg. and most preferably between about 1 mg/kg and 20 mg/kg, and the i.v. dose about 0.1 Ig/kg to about 100 $\mu$g/kg, preferably between about 0.1 mg/kg to 50 mg/kg. In each particular case, the doses are determined in accordance with the factors distinctive to the patient to be treated, such as age, weight, general state of health and other characteristics which can influence the efficacy of the compound according to the invention.

Furthermore, a compound of formula II may be administered as frequently as necessary in order to obtain the desired therapeutic effect. Some patients may respond rapidly to a higher or lower dose and may find much weaker maintenance doses adequate. For other patients, it may be necessary to have long-term treatments at the rate of 1 to 4 oral doses per day, preferably once to twice daily, in accordance with the physiological requirements of each particular patient. Generally, the active product may be administered orally 1 to 4 times per day. Of course, for other patients, it will be necessary to prescribe not more than one or two doses per day.

A compound of formula II exhibits marked pharmacological activities according to tests described in the literature which tests results are believed to correlate to pharmacological activity in humans and other mammals. The following pharmacological in vitro and in vivo test results are typical for characterizing a compound of formula II.

The following pharmacologic tests evaluate the inhibitory activity of a compound of formula II on fibrinogen-mediated platelet aggregation, fibrinogen binding to thrombin-stimulated platelets, and inhibition of ADP-induced ex-vivo platelet aggregation, and results of these tests correlate to the in-vivo inhibitory properties of a compound of formula II.

The Platelet Aggregation Assay is based on that described in *Blood* 66 (4), 946–952 (1985). The Fibrinogen-Binding Assay is essentially that of Ruggeri, Z. M., et al., *Proc. Nail. Acad. Sci. USA* 83, 5708–5712 (1986) and Plow, E. F., et al., *Proc. Natl. Acad Sci., USA* 82, 8057–8061 (1985). The Inhibition of ADP-lndticed ex-vivo Platelet Aggregation assay is based on that of Zucker, "Platelet Aggregation Measured by the Photoelectric Method", *Methods in Enzymology* 169, 117–133 (1989).

Platelet Aggregation Assay

Preparation of Fixed-activated Platelets

Platelets are isolated from human platelet concentrates using the gel-filtration technique as described by Marguerie, G. A. et al., *J. Biol. Chem.* 254, 5357–5363 (1979) and Ruggeri, Z. M. et al., *J. Clin. Invest.* 72, 1–12 (1983). The platelets are suspended at a concentration of $2 \times 10^8$ cells/mL in a modified calcium-free Tyrode's buffer containing 127 mM sodium chloride, 2 mM magnesium chloride, 0.42 mM $Na_2HPO_4$, 11.9 mM $NaHCO_3$, 2.9 mM KCl, 5.5 mM glucose, 10 mM HEPES, at a pH of 7.35 and 0.35% human serum albumin (HSA). These washed platelets are activated by addition of human a-thrombin at a final concentration of 2 units/in, followed by thrombin inhibitor 1–2581 at a final concentration of 40 $\mu$M. To the activated platelets is added paraformaldehyde to a final concentration of 0.50% and this incubated at room temperature for 30 minutes. The fixed activated platelets are then collected by centrifugation at 650×g for 15 minutes. The platelet pellets are washed four times with the above Tyrode's-0.35% HSA buffer and resuspended to $2 \times 10^8$ cells/mL in the same buffer.

Platelet Aggregation Assay

The fixed activated platelets are incubated with a selected dose of the compound to be tested for platelet aggregation inhibition for one minute andfaggregation initiated by addition of human fibrinogen to a final concentration of 250 $\mu$g/mL. A platelet aggregation profiler Model PAP-4 is used to record the platelet aggregation. The extent of inhibition of aggregation is expressed as the percentage of the rate of aggregation observed in the absence of inhibitor. $IC_{50}$, i.e., the amount of inhibitor required to reduce the aggregation rate by 50%, is then calculated for each compound (see, for example, Plow, E. F. et al., *Proc. Natl. Acad. Sci., USA* 82, 8057–8061 (1985)).

Fibrinogen-binding Assay

Platelets are washed free of plasma constituents by the albumin density-gradient technique of Walsh, P. N. et al., *Br. J. Haematol.* 281–296 (1977), as modified by Trapani-Lombardo, V. et al., *J. Clin Invest.* 76, 1950–1958 (1985). In each experimental mixture platelets in modified Tyrode's buffer (Ruggeri, Z. M. et al., *J. Clin. Invest.* 72, 1–12(1983)) are stimulated with human a-thrombin at 22–25° C. for 10 minutes ($3.125 \times 10^{11}$ platelets per liter and thrombin at 0.1 NIH units/mL). Hirudin is then added at a 25-fold excess (unit/unit) for 5 minutes before addition of the $^{125}$I-labeled fibrinogen and the compound to be tested. After these additions, the final platelet count in the mixture is $1 \times 10^{11}$/L. After incubation for an additional 30 minutes at 22–25° C., bound and free ligand are separated by centrifuging 50 $\mu$L of the mixture through 300 $\mu$L of 20% sucrose at 12,000×g for 4 minutes. The platelet pellet is then separated from the rest of the mixture to determine platelet-bound radioactivity. Nonspecific binding is measured in mixtures containing an excess of unlabeled ligand. When binding curves are analyzed by Scatchard analysis, nonspecific binding is derived as a fitted parameter from the binding isothern by means of a computerized program (Munson, P. J., *Methods Enzymol.* 92, 542–576 (1983)). To determine the concentration of each compound necessary to inhibit 50% of fibrinogen binding to thrombin-stimulated platelets ($IC_{50}$), each compound is tested at 6 or more concentrations with $^{125}$I-labeled fibrinogen held at 0.176 $\mu$mol/L (60 $\mu$g/mL). The $IC_{50}$ is derived by plotting residual fibrinogen binding against the logarithm of the sample compound's concentration.

Inhibition of ADP-Induced Ex-vivo Platelet Aggregation

Experimental Protocol

Control blood samples are obtained 5–10 minutes prior to administration of a test compound in mongrel dogs weighing from 10 to 20 Kg. The compound is administered intragasticly, via aqueous gavage, or orally, via gelatin capsule. Blood samples (5 ml) are then obtained at 30 minute intervals for 3 hours, and at 6, 12, and 24 hours after dosing. Each blood sample is obtained by venipuncture of the cephalic vein and is collected directly into a plastic syringe containing one part 3.8% trisodium citrate to nine parts blood.

Ex Vivo Canine Platelet Aggregation

The blood samples are centrifuged at 1000 rpm for 10 minutes to obtain platelet rich plasma (PRP). After removal of the PRP, the sample is centrifuged for an additional 10 minutes at 2000 rpm to obtain platelet poor plasma (PPP). Platelet count in the PRP is determined by using a Coulter Counter (Coulter Electronics, Hialeah, Fla.). If the concentration of platelets in the PRP is greater than 300,000 platelets/$\mu$L, then the PRP is diluted with PPP to adjust the platelet count to 300,000 platelets/$\mu$L. Aliquots of PRP (250 $\mu$L) are then placed in siliconized glass cuvettes (7.25×55 mm, Bio/Data Corp., Horsham, Pa.). Epinephrine (final concentration of 1 $\mu$M) is then added to the PRP, which is incubated for one minute at 37° C. A stimulator of platelet aggregation ADP at a final concentration of 10 $\mu$M, is then added to the PRP. Platelet aggregation is monitored spectrophotometrically utilizing a light transmission aggregometer (Bio/Data Platelet Aggregation Profiler, Model PAP-4, Bio/Data Corp., Horsham, Pa.). For the testing of a compound, the rate of change (slope) of light transmittance and the maximum light transmittance (maximum aggregation) is recorded in duplicate. Platelet aggregation data are reported as the percent decrease (mean±SEM) in slope or maximum aggregation as compared to data obtained from control PRP, which is prepared from blood samples obtained prior to administration of the test compound.

A compound of formula II exhibits marked activity in the foregoing tests and is considered useful in the prevention and treatment of thrombosis associated with certain disease states. Antithrombotic activity in the ex vivo canine platelet aggregation assay is predictive of such activity in humans (see, for example, Catalfamo, J. L., and Dodds, W. Jean, "Isolation of Platelets from Laboratory Animals", *Methods Enzynol.* 169, Part A, 27 (1989)). Results of testing of a compound of formula II by the above methods are presented in the Table 6 below. Also presented in the table are comparative test results for 4-4(piperidyl)butanoyl glycyl aspartyl tryptophan, i.e., the compound disclosed in European Patent Application Publication No. 0479,481.

TABLE 6

| Compound of Example Number | Inhibition of Fixed Platelet Aggregation ($IC_{50}$ $\mu$M) | Dose (mg/kg) | Inhibition of ADP-Induced ex-vivo Platelet Aggregation % Inhibition of ex-vivo Platelet Aggregation After Oral Administration | | | | |
|---|---|---|---|---|---|---|---|
| | | | 1 h | 3 h | 6 h | 12 h | 24 h |
| 15 | 0.097 | 5 | 100 | 100 | 100 | 98 | 50 |
| (Compound of EPA '481) | 0.047 | 5 | 53 | <20 | | | |

One skilled in the art will readily appreciate that the present invention is well adapted to carry out the objects of the invention, and obtain the ends and advantages mentioned, as well as those inherent therein. The compounds, compositions, and methods described herein are presented as representative of the preferred embodiments, or intended to be exemplary and not intended as limitations on the scope of the present invention.

What is claimed is:

1. A compound which is N-(N-t-butoxycarbonyl-N-ethylglycyl)-(L)-aspartic acid β-benzyl ester.

2. A compound which is N-[N-[N-[4-[N-benzyloxycarbonylpiperdin-4-yl]butanoyl]-N-ethylglycyl]-(L)-aspartyl β-benzyl ester]-(L)-β-cyclohexylalanine amide.

3. A compound which is 4-(4-piperidinebutylidenylcarboxylic acid.

4. A compound which is N-[N-[N-[3-[N-benzyloxycarbonyl-4-piperidin]propylidenylcarbonyl]-N-ethylglycyl]-(L)-aspartylβ-benzyl ester]-(L)-β-cyclohexylalanine amide.

5. A method for preparing a trifluoroacetic acid salt of formula

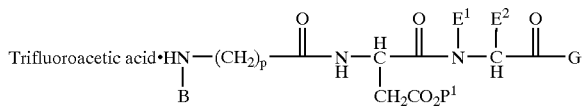

wherein

B is alkyl, cycloalkyl, cycloalkylalkyl, alkylcycloalkyl, alkylcycloalkylalkyl, aryl, aralkyl, alkylaryl, or alkylaralkyl;

$E^1$ is H;

$E^2$ is the α-carbon side chain of a naturally occuring α-amino acid, H, alkyl, cycloalkyl, cycloalkylalkyl, alkylcycloalkyl, alkylcycloalkylalkyl, aryl, substituted aryl, aralkyl, substitued aralkyl, heterocyclyl, substituted heterocyclyl, heterocyclylalkyl, substituted heterocyclylalkyl, or $E^1$ and $E^2$ taken together with the nitrogen and carbon atoms through which $E^1$ and $E^2$ are linked form a 4-, 5-, 6-, or 7-membered azacycloalkane ring;

G is $OR^1$ or $NR^1R^2$;

$R^1$ and $R^2$ are independently H, alkyl, cycloalkyl, cycloalkylalkyl, alkylcycloalkyl, alkylcycloalkylalkyl, aryl, aralkyl, alkylaryl, or alkylaralkyl;

p is 1 to 4; and $P^1$ is a carboxylic acid protecting group, comprising coupling compounds of the formulae

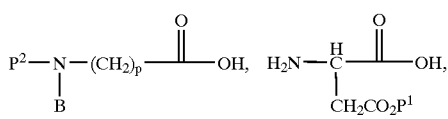

wherein $P^2$ is an acid labile amine protecting group, for a time and under conditions effective to form a first intermediary compound of formula

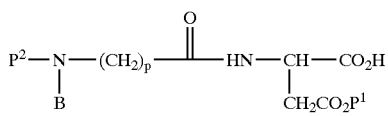

coupling a compound of formula

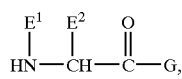

to the first intermediary compound for a time and under conditions effective to form a second intermediary compound of formula

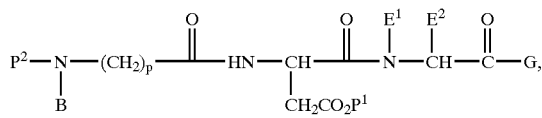

removing the $P^2$ protecting group from the second intermediary compound with trifluoroacetic acid for a time and under conditions effective to yield the trifluoroacetic acid salt, and isolating the trifluoroacetic acid salt.

6. The method of claim 5 wherein $P^1$ is a hydrogenation-labile carboxylic acid protecting group.

7. A compound of formula wherein $P^3$ is an amine protecting group;

B is alkyl, cycloalkyl, cycloalkylalkyl, alkylcycloalkyl, alkylcycloalkylalkyl, aryl, aralkyl, alkylaryl, or alkylaralkyl;

$P^1$ is a carboxylic acid protecting group;

$E^1$ is H;

$E^2$ is the a-carbon side chain of a naturally occuring a-amino acid, H, alkyl, cycloalkyl, cycloalkylalkyl, alkylcycloalkyl, alkylcycloalkylalkyl, aryl, substituted aryl, aralkyl, substitued aralkyl, heterocyclyl, substituted heterocyclyl, heterocyclylalkyl, substituted heterocyclylalkyl, or $E^1$ and $E^2$ taken together with the nitrogen and carbon atoms through which $E^1$ and $E^2$ are linked form a 4-, 5-, 6-, or 7-membered azacycloalkane ring;

G is $OR^1$ or $NR^1R^2$;

$R^1$ and $R^2$ are independently H, alkyl, cycloalkyl, cycloalkylalkyl, alkylcycloalkyl, alkylcycloalkylalkyl, aryl, aralkyl, alkylaryl, or alkylaralkyl; and p is 1–4.

8. A compound according to claim 7 wherein $P^1$ is a hydrogenation-labile carboxylic acid protecting group and $P^3$ is a hydrogenation-labile amine protecting group.

9. A compound according to claim 8 wherein

B is alkyl, cycloalkyl, cycloalkylalkyl, alkylcycloalkyl, alkylcycloalkylalkyl, aryl, aralkyl, alkylaryl or alkylaralkyl;

$E^1$ is H;

$E^2$ is H, alkyl, cycloalkyl, cycloalkylalkyl, alkylcycloalkyl, alkylcycloalkylalkyl, aryl, substituted aryl, aralkyl or substitued aralkyl;

L is $OR^1$ or $NR^1R^2$;

$R^1$ and $R^2$ are independently H, alkyl, cycloalkyl, cycloalkylalkyl, alkylcycloalkyl, alkylcycloalkylalkyl, aryl, aralkyl, alkylaryl or alkylaralkyl; and p is 1 or 2.

10. A compound according to claim 9 wherein

B is alkyl, cycloalkyl, cycloalkylalkyl, alkylcycloalkyl or alkylcycloalkylalkyl; and $E^2$ is H, alkyl, cycloalkyl, cycloalkylalkyl, alkylcycloalkyl or alkylcycloalkylalkyl.

11. A compound according to claim 10 wherein

B is alkyl;

$E^2$ is alkyl, cycloalkyl or cycloalkylalkyl;

$R^1$ and $R^2$ are independently H, alkyl, cycloalkyl, cycloalkylalkyl, alkylcycloalkyl or alkylcycloalkylalkyl; and p is 1.

12. A compound according to claim 11 wherein $P^3$ is benzyloxycarbonyl;

B is ethyl;

$P^1$ is benzyl;

$E^2$ is cyclohexylmethyl: and

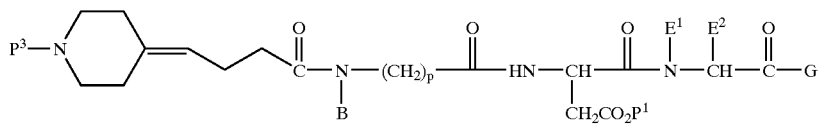

G is NH$_2$.

13. A method of preparing a compound of formula:

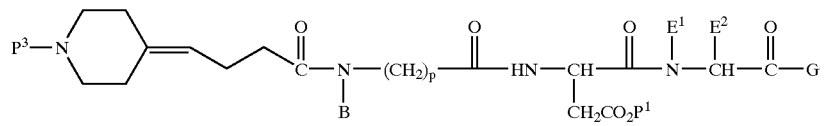

wherein
- P$^3$ is an amine protecting group;
- B is alkyl, cycloalkyl, cycloalkylalkyl, alkylcycloalkyl, alkylcycloalkylalkyl, aryl, aralkyl, alkylaryl, or alkylaralkyl;
- P$^1$ is a carboxylic protecting group;
- E$^1$ is H;
- E$^2$ is the a-carbon side chain of a naturally occuring a-amino acid, H, alkyl, cycloalkyl, cycloalkylalkyl, alkylcycloalkyl, alkylcycloalkylalkyl, aryl, substituted aryl, aralkyl, substitued aralkyl, heterocyclyl, substituted heterocyclyl, heterocyclylalkyl, substituted heterocyclylalkyl, or E$^1$ and E$^2$ taken together with the nitrogen and carbon atoms through which E$^1$ and E$^2$ are linked form a 4-, 5-, 6-, or 7-membered azacycloalkane ring;
- G is OR$^1$ or NR$^1$R$^2$;
- R$^1$ and R$^2$ are independently H, alkyl, cycloalkyl, cycloalkylalkyl, alkylcycloalkyl, alkylcycloalkylalkyl, aryl, aralkyl, alkylaryl, or alkylaralkyl, and p is 1–4;

comprising coupling a ((4-Piperidin)butylidenylcarboxylic acid) compound of formula

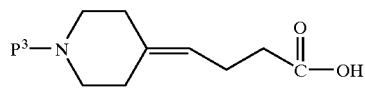

with a tripeptide of formula

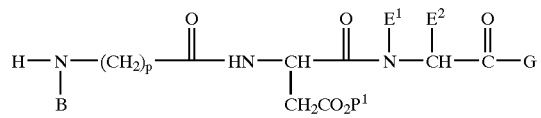

or an acid addition salt thereof, for a time and under conditions effective to generate the compound of formula:

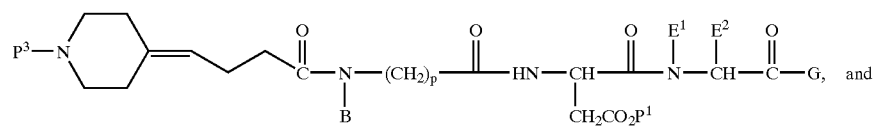

and isolating the compound of formula:

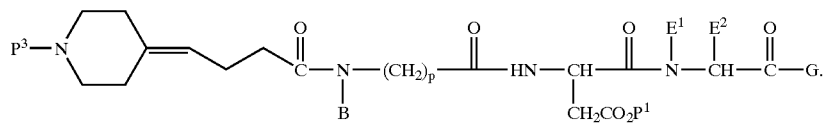

14. The method of claim 13 wherein P$^1$ is a hydrogenation-labile carboxylic acid protecting group and P$^3$ is a hydrogenation-labile amine protecting group.

15. A compound formula

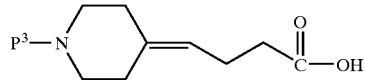

wherein P$^3$ is an amine protecting group.

16. A compound according to claim 15 wherein P$^3$ is a hydrogenation-labile amine protecting group.

17. A compound according to claim 16 wherein P$^3$ is benzyloxycarbonyl.

* * * * *

SEQUENCE LISTING

<160> NUMBER OF SEQ ID NOS: 4

<210> SEQ ID NO 1
<211> LENGTH: 12
<212> TYPE: PRT
<213> ORGANISM: Artificial sequence
<220> FEATURE:
<223> OTHER INFORMATION: synthetic peptide inhibiting aggregation of
      activated platelets

<400> SEQUENCE: 1

His His Leu Gly Gly Ala Lys Gln Ala Gly Asp Val
1               5                   10

<210> SEQ ID NO 2
<211> LENGTH: 4
<212> TYPE: PRT
<213> ORGANISM: artificial sequence
<220> FEATURE:
<223> OTHER INFORMATION: synthetic peptide capable of inhibiting
      thrombin-induced platelet aggregation

<400> SEQUENCE: 2

Arg Gly Asp Ser
1

<210> SEQ ID NO 3
<211> LENGTH: 5
<212> TYPE: PRT
<213> ORGANISM: artificial sequence
<220> FEATURE:
<223> OTHER INFORMATION: synthetic peptide capable of inhibiting
      thrombin-induced platelet aggregation

<400> SEQUENCE: 3

Gly Arg Gly Asp Ser
1               5

<210> SEQ ID NO 4
<211> LENGTH: 4
<212> TYPE: PRT
<213> ORGANISM: Artificial sequence
<220> FEATURE:
<223> OTHER INFORMATION: synthetic peptide capable of inhibiting binding
      of fibrinogen to platelets

<400> SEQUENCE: 4

Gly Pro Arg Pro
1